US012611180B2

(12) United States Patent
Dehghan et al.

(10) Patent No.: US 12,611,180 B2
(45) Date of Patent: Apr. 28, 2026

(54) METHOD AND SYSTEM FOR CROSS-REFERENCING OF TWO-DIMENSIONAL (2D) ULTRASOUND SCANS OF A TISSUE VOLUME

(71) Applicant: Exo Imaging, Inc., Santa Clara, CA (US)

(72) Inventors: Masood Dehghan, Edmonton (CA); Xuebin Qin, Edmonton (CA); Dornoosh Zonoobi, Edmonton (CA)

(73) Assignee: Exo Imaging, Inc., Santa Clara, CA (US)

( * ) Notice: Subject to any disclaimer, the term of this patent is extended or adjusted under 35 U.S.C. 154(b) by 18 days.

(21) Appl. No.: 18/556,854

(22) PCT Filed: Mar. 2, 2023

(86) PCT No.: PCT/US2023/063566
§ 371 (c)(1),
(2) Date: Oct. 23, 2023

(87) PCT Pub. No.: WO2023/183699
PCT Pub. Date: Sep. 28, 2023

(65) Prior Publication Data
US 2024/0164755 A1 May 23, 2024

Related U.S. Application Data

(60) Provisional application No. 63/323,515, filed on Mar. 25, 2022.

(51) Int. Cl.
*A61B 8/00* (2006.01)
*G16H 30/40* (2018.01)
*G16H 50/50* (2018.01)

(52) U.S. Cl.
CPC .............. *A61B 8/463* (2013.01); *A61B 8/466* (2013.01); *A61B 8/5207* (2013.01);
(Continued)

(58) Field of Classification Search
None
See application file for complete search history.

(56) References Cited

U.S. PATENT DOCUMENTS 5,529,070 A * 6/1996 Augustine ........... G01S 15/8993
600/443
5,787,889 A * 8/1998 Edwards ................. A61B 8/14
600/443

(Continued)

OTHER PUBLICATIONS

Exo Imaging, Inc., International Search Report and Written Opinion, PCT/US2023/063566, Sep. 27, 2023, 16 pgs.

*Primary Examiner* — Nyrobi Celestine
(74) *Attorney, Agent, or Firm* — Morgan, Lewis & Bockius LLP

(57) ABSTRACT

A method for cross-referencing of 2D ultrasound scans of a tissue volume comprises generating first and second 2D representations of a target anatomy, respectively, from first and second series of 2D ultrasound images of the tissue volume generated. The method includes generating first and second simulated 2D representations of the target anatomy, respectively, from the second and first series of 2D ultrasound images. The 2D and simulated 2D representations are processed to at least substantially match pixel positions in the 2D and simulated 2D representations associated with the target anatomy. The method includes determining first and second correspondence transformation matrices from the processed 2D and simulated 2D representations, and using the first and second correspondence transformation matrices to determine, for a location in the second series of 2D ultrasound images associated with the target anatomy, a
(Continued)

corresponding location in the first series of 2D ultrasound images.

21 Claims, 12 Drawing Sheets

(52) U.S. Cl.
CPC ........... *A61B 8/5246* (2013.01); *G16H 30/40* (2018.01); *G16H 50/50* (2018.01)

(56) References Cited

U.S. PATENT DOCUMENTS

| | | | | |
|---|---|---|---|---|
| 6,102,861 | A * | 8/2000 | Avila | G01S 7/52034 |
| | | | | 600/443 |
| 2002/0198452 | A1 * | 12/2002 | Taylor | G06T 17/00 |
| | | | | 600/426 |
| 2006/0241432 | A1 * | 10/2006 | Herline | A61B 8/483 |
| | | | | 600/437 |
| 2007/0230758 | A1 | 10/2007 | Fan et al. | |
| 2012/0271162 | A1 * | 10/2012 | Liao | G06T 7/285 |
| | | | | 600/424 |
| 2013/0018265 | A1 | 1/2013 | Kim et al. | |
| 2013/0094742 | A1 * | 4/2013 | Feilkas | A61B 6/584 |
| | | | | 382/131 |
| 2013/0165789 | A1 * | 6/2013 | Yao | A61B 8/5223 |
| | | | | 600/443 |
| 2017/0367766 | A1 * | 12/2017 | Mahfouz | A61F 2/3859 |
| 2018/0301063 | A1 | 10/2018 | Beudeker et al. | |
| 2019/0142528 | A1 * | 5/2019 | Vertikov | A61B 1/00172 |
| | | | | 600/424 |
| 2020/0113543 | A1 | 4/2020 | Wasielewski | |
| 2023/0026942 | A1 * | 1/2023 | Meral | A61B 8/465 |
| 2023/0127935 | A1 * | 4/2023 | Chen | A61B 8/5238 |
| | | | | 382/131 |
| 2024/0193764 | A1 * | 6/2024 | Speter | A61B 8/0891 |
| 2025/0169892 | A1 * | 5/2025 | Bowman | A61B 17/155 |

* cited by examiner

100

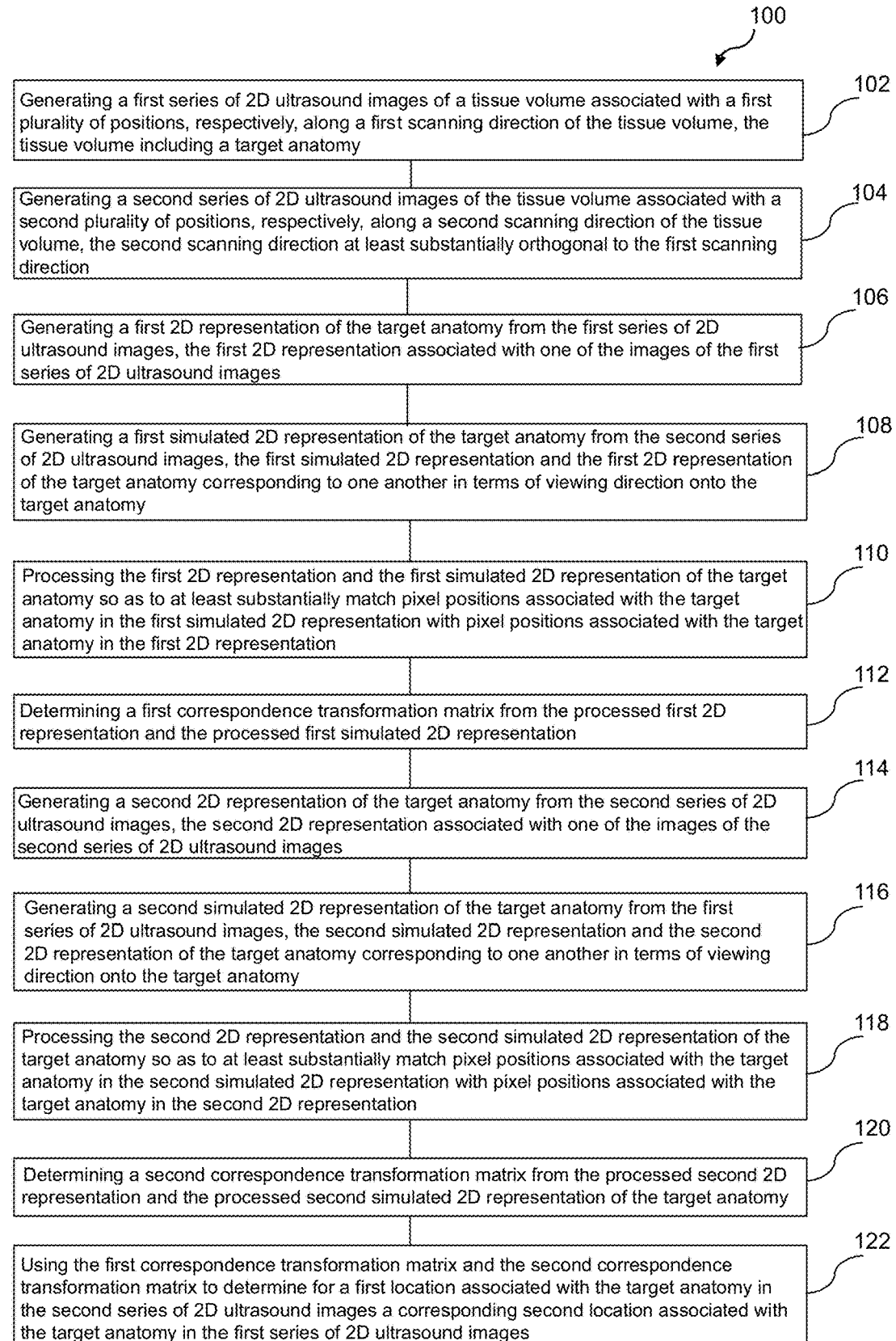

Generating a first series of 2D ultrasound images of a tissue volume associated with a first plurality of positions, respectively, along a first scanning direction of the tissue volume, the tissue volume including a target anatomy — 102

Generating a second series of 2D ultrasound images of the tissue volume associated with a second plurality of positions, respectively, along a second scanning direction of the tissue volume, the second scanning direction at least substantially orthogonal to the first scanning direction — 104

Generating a first 2D representation of the target anatomy from the first series of 2D ultrasound images, the first 2D representation associated with one of the images of the first series of 2D ultrasound images — 106

Generating a first simulated 2D representation of the target anatomy from the second series of 2D ultrasound images, the first simulated 2D representation and the first 2D representation of the target anatomy corresponding to one another in terms of viewing direction onto the target anatomy — 108

Processing the first 2D representation and the first simulated 2D representation of the target anatomy so as to at least substantially match pixel positions associated with the target anatomy in the first simulated 2D representation with pixel positions associated with the target anatomy in the first 2D representation — 110

Determining a first correspondence transformation matrix from the processed first 2D representation and the processed first simulated 2D representation — 112

Generating a second 2D representation of the target anatomy from the second series of 2D ultrasound images, the second 2D representation associated with one of the images of the second series of 2D ultrasound images — 114

Generating a second simulated 2D representation of the target anatomy from the first series of 2D ultrasound images, the second simulated 2D representation and the second 2D representation of the target anatomy corresponding to one another in terms of viewing direction onto the target anatomy — 116

Processing the second 2D representation and the second simulated 2D representation of the target anatomy so as to at least substantially match pixel positions associated with the target anatomy in the second simulated 2D representation with pixel positions associated with the target anatomy in the second 2D representation — 118

Determining a second correspondence transformation matrix from the processed second 2D representation and the processed second simulated 2D representation of the target anatomy — 120

Using the first correspondence transformation matrix and the second correspondence transformation matrix to determine for a first location associated with the target anatomy in the second series of 2D ultrasound images a corresponding second location associated with the target anatomy in the first series of 2D ultrasound images — 122

Sagittal Scan

Transverse Scan

Thyroid SAG Sweep

Thyroid TRX Sweep

METHOD AND SYSTEM FOR CROSS-REFERENCING OF TWO-DIMENSIONAL (2D) ULTRASOUND SCANS OF A TISSUE VOLUME

CROSS REFERENCE TO RELATED APPLICATION

This Application is a United States National Stage Application filed under 35 U.S.C. § 371 of PCT Patent Application Serial No. PCT/US23/63566 filed on Mar. 2, 2023, which claims the benefit of and priority to U.S. Patent Application No. 63/323,515 filed on Mar. 25, 2022, each of which is hereby incorporated by reference in its entirety.

TECHNICAL FIELD

The present invention generally relates to a method and a system for cross-referencing of two-dimensional (2D) ultrasound scans of a tissue volume, and more particularly, of two sweeps of 2D ultrasound images of the tissue volume taken from orthogonal or substantially orthogonal views or planes.

BACKGROUND

Two-dimensional (2D) ultrasound (US) imaging is safe, inexpensive and widely used in medical practices, as well as having real-time and high resolution capabilities. Conventional 2D ultrasound imaging techniques may be configured to extract a 2D ultrasound image (which may also be referred to as a cross-sectional image, an image plane/frame or a B-mode/B-scan image) of the anatomy or tissue volume scanned by an ultrasound probe.

However, conventional 2D ultrasound imaging techniques have the inherent limitation of relying upon a 2D image to depict three-dimensional (3D) anatomy. A transducer may often be manually manipulated (moved) by an operator to obtain a 2D image (or series of 2D images, also known as 2D sweep or freehand sweep) of a body organ to cover the 3D anatomy.

In 3D imaging modalities (e.g., magnetic resonance imaging (MRI) or computed tomography (CT)), images may be taken with known 3D pixel spacing, which enables multiplanar reformatted imaging: scan data can be visualized in the transverse (or axial), coronal, or sagittal plane, depending on the diagnostic task. In freehand ultrasound, however, only pixel spacing in the imaging plane (x-y) is available and the pixel spacing in the out-of-plane direction (z-direction) may not be available. Thus, if an ultrasound scan is taken in a transverse plane, simple projection of image in sagittal view may result in poor quality and low-resolution sagittal scan that may not be usable for diagnostic imaging.

An inherent limitation of ultrasound imaging is that it may have high resolution in the imaging plane (high axial and lateral resolution) but not in the out-of-plane direction. Therefore, in clinical standard evaluation, it is common to take two sweeps of 2D ultrasound images from orthogonal directions to better capture the 3D anatomy in high resolution. While this may help in getting the image, matching these two views and finding the corresponding point in another view is a challenging problem because the freehand sweeps are taken by hand and there is no reference point for matching the images. This problem is also referred to as registration of two views in the field of computer vision and medical imaging.

In clinical settings, the images from two views are usually mentally cross-referenced (or registered) by an expert radiologist/sonographer to form a subjective impression of the 3D anatomy and/or pathology. This practice is time-consuming, inefficient and puts high cognitive load on the radiologists and often leads to variability and inconsistency in measurements and diagnoses.

The problem will be further exemplified herein below with reference to FIG. 4 in the context of sonography of the thyroid gland, without loss of generality.

FIG. 4 shows, in (a) and (b) a schematic of the (human) thyroid gland (labelled "T"). The arrows in (a) and (b) show a scanning direction of an ultrasound probe in the transverse (TRX) and sagittal (SAG) planes, respectively. (c) and (d) are sample TRX and SAG thyroid ultrasound sweeps with manually labelled thyroid lobe boundary overlay (contours labelled "C1" and "C2").

As part of routine thyroid ultrasonography workflow, clinicians may sequentially scan both left and right lobes of the thyroid gland. Scanning for each side (e.g., left lobe as shown in FIG. 4) may include scanning in the transverse (TRX) plane (as shown in (a) of FIG. 4) and scanning in the sagittal (SAG) plane (as shown in (b) of FIG. 4). For example, scanning for each side may be done first in the transverse (TRX) plane followed by the scan in the sagittal (SAG) plane.

The clinicians may then view patient scans containing transverse (TRX) sweeps and sagittal (SAG) sweeps of the thyroid gland. Transverse images (such as the image shown in (c) of FIG. 4) may often be inspected first for the appearance of nodules or suspected lesions. When nodules are found, there may often be a need to manually locate each nodule in a corresponding image taken along the sagittal view (such as the image shown in (d) of FIG. 4) to inspect it in both views. To do that, clinicians may have to scroll through all frames of the SAG scan and localize the same nodule. Regions of interest (ROI) or landmarks may then be annotated and measured on both views and recorded for later inspection. This task is of high-cognitive load, and is time-consuming.

Accordingly, there is a need to provide a method and a system for cross-referencing of two-dimensional (2D) ultrasound scans of a tissue volume that seek to overcome, or at least ameliorate, one or more of the deficiencies associated with conventional methods and systems, and in particular, with respect to a freehand ultrasound scanning of the tissue volume. It is against this background that the present invention has been developed

SUMMARY

According to a first aspect of the present invention, there is provided a method for cross-referencing of two-dimensional (2D) ultrasound scans of a tissue volume, the method comprising:

generating a first series of 2D ultrasound images of a tissue volume associated with a first plurality of positions, respectively, along a first scanning direction of the tissue volume, the tissue volume including a target anatomy;

generating a second series of 2D ultrasound images of the tissue volume associated with a second plurality of positions, respectively, along a second scanning direction of the tissue volume, wherein the second scanning direction is at least substantially orthogonal to the first scanning direction;

generating a first 2D representation of the target anatomy from the first series of 2D ultrasound images, the first 2D representation associated with one of the images of the first series of 2D ultrasound images;

generating a first simulated 2D representation of the target anatomy from the second series of 2D ultrasound images, the first simulated 2D representation and the first 2D representation of the target anatomy corresponding to one another in terms of viewing direction onto the target anatomy;

processing the first 2D representation and the first simulated 2D representation of the target anatomy so as to at least substantially match pixel positions associated with the target anatomy in the first simulated 2D representation with pixel positions associated with the target anatomy in the first 2D representation;

determining a first correspondence transformation matrix from the processed first 2D representation and the processed first simulated 2D representation of the target anatomy;

generating a second 2D representation of the target anatomy from the second series of 2D ultrasound images, the second 2D representation associated with one of the images of the second series of 2D ultrasound images;

generating a second simulated 2D representation of the target anatomy from the first series of 2D ultrasound images, the second simulated 2D representation and the second 2D representation of the target anatomy corresponding to one another in terms of viewing direction onto the target anatomy;

processing the second 2D representation and the second simulated 2D representation of the target anatomy so as to at least substantially match pixel positions associated with the target anatomy in the second simulated 2D representation with pixel positions associated with the target anatomy in the second 2D representation;

determining a second correspondence transformation matrix from the processed second 2D representation and the processed second simulated 2D representation of the target anatomy; and using the first correspondence transformation matrix and the second correspondence transformation matrix to determine for a first location associated with the target anatomy in the second series of 2D ultrasound images a corresponding second location associated with the target anatomy in the first series of 2D ultrasound images.

In various embodiments, using the first correspondence transformation matrix and the second correspondence transformation matrix to determine the second location comprises:

applying a first function of the first correspondence transformation matrix and second correspondence transformation matrix to pixel coordinates corresponding to the first location so as to obtain pixel coordinates corresponding to the second location.

In various embodiments, the method further comprises:

using the first correspondence transformation matrix and the second correspondence transformation matrix to determine for a third location associated with the target anatomy in the first series of 2D ultrasound images a corresponding fourth location associated with the target anatomy in the second series of 2D ultrasound images.

In various embodiments, using the first correspondence transformation matrix and the second correspondence transformation matrix to determine the fourth location comprises:

applying a second function of the first correspondence transformation matrix and second correspondence transformation matrix to pixel coordinates corresponding to the third location so as to obtain pixel coordinates corresponding to the fourth location.

In various embodiments, the method further comprises:

generating a first plurality of binary segmentation masks from the first series of 2D ultrasound images, each binary segmentation mask of the first plurality of binary segmentation masks corresponding to a respective one of the 2D ultrasound images of the first series of 2D ultrasound images; and generating a second plurality of binary segmentation masks from the second series of 2D ultrasound images, each binary segmentation mask of the second plurality of binary segmentation masks corresponding to a respective one of the 2D ultrasound images of the second series of 2D ultrasound images, wherein the first 2D representation of the target anatomy is generated from one of the binary segmentation masks of the first plurality of binary segmentation masks, and wherein the second 2D representation of the target anatomy is generated from one of the binary segmentation masks of the second plurality of binary segmentation masks.

In various embodiments, the first 2D representation of the target anatomy corresponds to a largest binary segmentation mask among the first plurality of binary segmentation masks, and the second 2D representation of the target anatomy corresponds to a largest binary segmentation mask among the second plurality of binary segmentation masks.

In various embodiments, generating the first simulated 2D representation of the target anatomy from the second series of 2D ultrasound images comprises generating the first simulated 2D representation of the target anatomy from the second plurality of binary segmentation masks, and generating the second simulated 2D representation of the target anatomy from the first series of 2D ultrasound images comprises generating the second simulated 2D representation of the target anatomy from the first plurality of binary segmentation masks.

In various embodiments, processing the first 2D representation comprises generating a first signed distance map from the first 2D representation, and processing the second 2D representation comprises generating a second signed distance map from the second 2D representation.

In various embodiments, processing the first simulated 2D representation comprises scaling a width of the first simulated 2D representation so as to match a width of the first 2D representation, and processing the second simulated 2D representation comprises scaling a width of the second simulated 2D representation so as to match a width of the second 2D representation.

In various embodiments, processing the first simulated 2D representation further comprises determining and sampling contour pixels associated with a contour of the target anatomy from the scaled first simulated 2D representation, and processing the second simulated 2D representation further comprises determining and sampling contour pixels associated with a contour of the target anatomy from the scaled second simulated 2D representation.

In various embodiments, processing the first simulated 2D representation further comprises sampling a first subset of pixels from the scaled first simulated 2D representation, and processing the second simulated 2D representation further comprises sampling a second subset of pixels from the scaled second simulated 2D representation.

In various embodiments, processing the first simulated 2D representation further comprises estimating coarse shifts between the scaled first simulated 2D representation and the first 2D representation using the first signed distance map and the first sampled subset of pixels, and processing the second simulated 2D representation further comprises estimating coarse shifts between the scaled second simulated 2D representation and the second 2D representation using the second signed distance map and the sampled second subset of pixels.

In various embodiments, determining the first correspondence transformation matrix comprises estimating a scale and translation between the scaled first simulated 2D representation and the first 2D representation by minimizing a first alignment cost defined as a first cost function with respect to the first correspondence transformation matrix; and determining the second correspondence transformation matrix comprises estimating a scale and translation between the scaled second simulated 2D representation and the second 2D representation by minimizing a second alignment cost defined as a second cost function with respect to the second correspondence transformation matrix.

In various embodiments, the first scanning direction corresponds to a transverse scan of the tissue volume and the second scanning direction corresponds to a sagittal scan of the tissue volume.

According to a second aspect of the present invention, there is provided a system for cross-referencing of two-dimensional ultrasound scans of a tissue volume, the system comprising:

a memory; and
at least one processor communicatively coupled to the memory and the ultrasound transducer, and configured to:
generate a first series of 2D ultrasound images of a tissue volume associated with a first plurality of positions, respectively, along a first scanning direction of the tissue volume, the tissue volume including a target anatomy;
generate a second series of 2D ultrasound images of the tissue volume associated with a second plurality of positions, respectively, along a second scanning direction of the tissue volume, wherein the second scanning direction is at least substantially orthogonal to the first scanning direction;
generate a first 2D representation of the target anatomy from the first series of 2D ultrasound images, the first 2D representation associated with one of the images of the first series of 2D ultrasound images;
generate a first simulated 2D representation of the target anatomy from the second series of 2D ultrasound images, the first simulated 2D representation and the first 2D representation of the target anatomy corresponding to one another in terms of viewing direction onto the target anatomy;
process the first 2D representation and the first simulated 2D representation of the target anatomy so as to at least substantially match pixel positions associated with the target anatomy in the first simulated 2D representation with pixel positions associated with the target anatomy in the first 2D representation;
determine a first correspondence transformation matrix from the processed first 2D representation and the processed first simulated 2D representation of the target anatomy;
generate a second 2D representation of the target anatomy from the second series of 2D ultrasound images, the second 2D representation associated with one of the images of the second series of 2D ultrasound images;
generate a second simulated 2D representation of the target anatomy from the first series of 2D ultrasound images, the second simulated 2D representation and the second 2D representation of the target anatomy corresponding to one another in terms of viewing direction onto the target anatomy;
process the second 2D representation and the second simulated 2D representation of the target anatomy so as to at least substantially match pixel positions associated with the target anatomy in the second simulated 2D representation with pixel positions associated with the target anatomy in the second 2D representation;
determine a second correspondence transformation matrix from the processed second 2D representation and the processed second simulated 2D representation of the target anatomy; and
use the first correspondence transformation matrix and the second correspondence transformation matrix to determine for a first location associated with the target anatomy in the second series of 2D ultrasound images a corresponding second location associated with the target anatomy in the first series of 2D ultrasound images.

In various embodiments, when the at least one processor uses the first correspondence transformation matrix and the second correspondence transformation matrix to determine the second location, the at least one processor is configured to:
apply a first function of the first correspondence transformation matrix and second correspondence transformation matrix to pixel coordinates corresponding to the first location so as to obtain pixel coordinates corresponding to the second location.

In various embodiments, the at least one processor is further configured to:
use the first correspondence transformation matrix and the second correspondence transformation matrix to determine for a third location associated with the target anatomy in the first series of 2D ultrasound images a corresponding fourth location associated with the target anatomy in the second series of 2D ultrasound images.

In various embodiments, when the at least one processor uses the first correspondence transformation matrix and the second correspondence transformation matrix to determine the fourth location, the at least one processor is configured to:
apply a second function of the first correspondence transformation matrix and second correspondence transformation matrix to pixel coordinates corresponding to the third location so as to obtain pixel coordinates corresponding to the fourth location.

In various embodiments, the at least one processor is further configured to:
generate a first plurality of binary segmentation masks from the first series of 2D ultrasound images, each binary segmentation mask of the first plurality of binary segmentation masks corresponding to a respective one of the 2D ultrasound images of the first series of 2D ultrasound images; and
generate a second plurality of binary segmentation masks from the second series of 2D ultrasound images, each binary segmentation mask of the second plurality of binary segmentation masks corresponding to a respective one of the 2D ultrasound images of the second series of 2D ultrasound images, wherein the first 2D representation of the target anatomy is generated from one of the binary segmentation masks of the first plurality of binary segmentation masks, and wherein the second 2D representation of the target anatomy is generated from one of the binary segmentation masks of the second plurality of binary segmentation masks.

In various embodiments, the first 2D representation of the target anatomy corresponds to a largest binary segmentation mask among the first plurality of binary segmentation masks, and the second 2D representation of the target anatomy corresponds to a largest binary segmentation mask among the second plurality of binary segmentation masks.

In various embodiments, the first scanning direction corresponds to a transverse scan of the tissue volume and the second scanning direction corresponds to a sagittal scan of the tissue volume.

In various embodiments, the system further comprises an ultrasound transducer communicatively coupled to the memory and the at least one processor, wherein the at least one processor is configured to: generate the first series of 2D ultrasound images based on a first series of ultrasound waves acquired by the ultrasound transducer positioned at the first plurality of positions with respect to a first plurality of time instances; and generate the second series of 2D ultrasound images based on a second series of ultrasound waves acquired by the ultrasound transducer positioned at the second plurality of positions with respect to a second plurality of time instances.

According to a third aspect of the present invention, there is provided a computer program product, embodied in one or more non-transitory computer-readable storage mediums, comprising instructions executable by at least one processor to perform a method for cross-referencing of two-dimensional ultrasound scans of a tissue volume, the method comprising:

generating a first series of 2D ultrasound images of a tissue volume associated with a first plurality of positions, respectively, along a first scanning direction of the tissue volume, the tissue volume including a target anatomy;

generating a second series of 2D ultrasound images of the tissue volume associated with a second plurality of positions, respectively, along a second scanning direction of the tissue volume, wherein the second scanning direction is at least substantially orthogonal to the first scanning direction;

generating a first 2D representation of the target anatomy from the first series of 2D ultrasound images, the first 2D representation associated with one of the images of the first series of 2D ultrasound images;

generating a first simulated 2D representation of the target anatomy from the second series of 2D ultrasound images, the first simulated 2D representation and the first 2D representation of the target anatomy corresponding to one another in terms of viewing direction onto the target anatomy;

processing the first 2D representation and the first simulated 2D representation of the target anatomy so as to at least substantially match pixel positions associated with the target anatomy in the first simulated 2D representation with pixel positions associated with the target anatomy in the first 2D representation;

determining a first correspondence transformation matrix from the processed first 2D representation and the processed first simulated 2D representation of the target anatomy;

generating a second 2D representation of the target anatomy from the second series of 2D ultrasound images, the second 2D representation associated with one of the images of the second series of 2D ultrasound images;

generating a second simulated 2D representation of the target anatomy from the first series of 2D ultrasound images, the second simulated 2D representation and the second 2D representation of the target anatomy corresponding to one another in terms of viewing direction onto the target anatomy;

processing the second 2D representation and the second simulated 2D representation of the target anatomy so as to at least substantially match pixel positions associated with the target anatomy in the second simulated 2D representation with pixel positions associated with the target anatomy in the second 2D representation;

determining a second correspondence transformation matrix from the processed second 2D representation and the processed second simulated 2D representation of the target anatomy; and using the first correspondence transformation matrix and the second correspondence transformation matrix to determine for a first location associated with the target anatomy in the second series of 2D ultrasound images a corresponding second location associated with the target anatomy in the first series of 2D ultrasound images.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes and may not have been selected to delineate or circumscribe the inventive subject matter.

BRIEF DESCRIPTION OF THE DRAWINGS

Embodiments of the present invention will be better understood and readily apparent to one of the ordinary skill in the art from the following written description, by way of example only, and in conjunction with the drawings.

FIG. 1 depicts a schematic flow diagram of a method for cross-referencing of 2D ultrasound scans of a tissue volume according to various embodiments of the present invention.

DESCRIPTION OF IMPLEMENTATIONS

Figure 2:
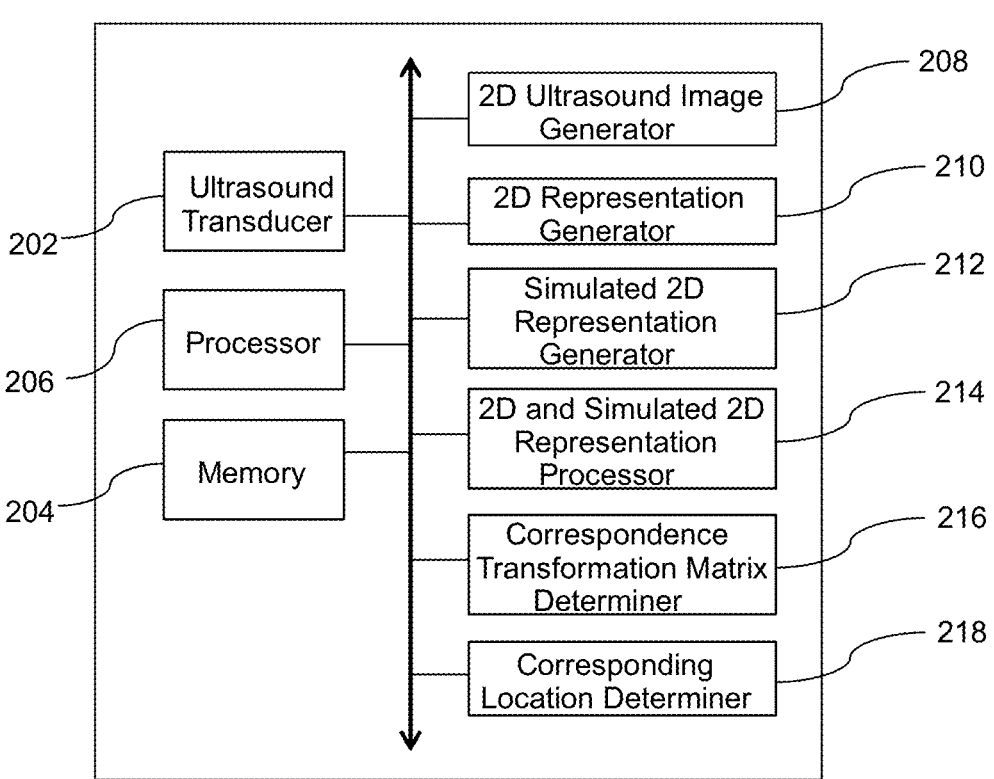
FIG. 2 depicts a schematic block diagram of a system for cross-referencing of 2D ultrasound scans of a tissue volume according to various embodiments of the present invention, such as corresponding to the method as depicted in FIG. 1.

Various embodiments of the present invention provide a method (computer-implemented method) and a system including a memory and at least one processor communicatively coupled to the memory) for cross-referencing of two-dimensional (2D) ultrasound scans of a tissue volume, and more particularly, of two sweeps of 2D ultrasound images of the tissue volume taken from orthogonal or substantially orthogonal views or planes.

As mentioned in the background, two-dimensional (2D) ultrasound imaging is safe, inexpensive and widely used in medical practices. However, in conventional ultrasound imaging, registration (or cross-referencing) of images obtained from two different views is done mentally by an expert radiologist/sonographer to form a subjective impression of the 3D anatomy and/or pathology, which practice is time-consuming, inefficient and puts high cognitive load on the radiologists and often leads to variability and incorrect diagnoses.

Accordingly, various embodiments of the present invention provide a method and a system that achieve more efficient and/or reliable cross-referencing (registration) of two 2D ultrasound scans of a tissue volume that are taken from two different views. The cross-referencing may find the corresponding points from one plane to the other plane. In other words, cross-referencing may map a given point on the one plane or view (e.g., transverse (TRX) view) to the corresponding point on the other plane or view (e.g., sagittal (SAG) view).

Various embodiments of the invention may thus bridge the gap between 2D ultrasound and 3D imaging modalities (e.g., computed tomography (CT) or magnetic resonance imaging (MRI)) by providing a correspondence between points in different views. Examples of clinical applications may include but are not limited to: Cardiology, Vascular Imaging, Prostate, Bladder and Thyroid imaging.

Various embodiments of the invention may benefit the clinical workflow by simplifying measurement, screening and/or monitoring of an organ over time as they make matching of the anatomy easier and more reliable.

FIG. 1 depicts a schematic flow diagram of a method 100 (computer-implemented method) for cross-referencing of two-dimensional (2D) ultrasound scans of a tissue volume (including a target anatomy) using at least one processor, according to various embodiments of the invention.

The method 100 comprises a step 102 of generating a first series (or sequence or set) of 2D ultrasound images (which may also be interchangeably referred to as a cross-sectional image, an image plane, an image frame/slice or a B-mode/B-scan image) of the tissue volume associated with a first plurality of positions, respectively, along a first scanning direction of the tissue volume, the tissue volume including a target anatomy.

The method 100 further comprises a step 104 of generating a second series (or sequence or set) of 2D ultrasound images of the tissue volume associated with a second plurality of positions, respectively, along a second scanning direction of the tissue volume, wherein the second scanning direction is at least substantially orthogonal to the first scanning direction. In various embodiments, the term "at least substantially orthogonal" as used herein in connection with two directions (e.g., the "first scanning direction" and the "second scanning direction") may be understood to mean that the two directions are orthogonal to one another, or almost orthogonal to one another, for example having a deviation from orthogonality of less than or equal to 10 degrees, e.g. less than or equal to 5 degrees, e.g. less than or equal to 2 degrees, e.g. less than or equal to 1 degree.

In relation to step 102, the first series of 2D ultrasound images may be respectively generated based on a first series of ultrasound waves acquired by an ultrasound transducer positioned at the first plurality of positions with respect to a first plurality of time instances. Alternatively, the first series of 2D ultrasound images may be respectively generated based on first image data stored in a memory that is related to a first series of ultrasound waves acquired by an ultrasound transducer positioned at the first plurality of positions with respect to a first plurality of time instances.

Similarly, in relation to step 104, the second series of 2D ultrasound images may be respectively generated based on a first series of ultrasound waves acquired by the ultrasound transducer positioned at the second plurality of positions with respect to a second plurality of time instances. Alternatively, the second series of 2D ultrasound images may be respectively generated based on second image data stored in the memory that is related to a second series of ultrasound waves acquired by the ultrasound transducer positioned at the second plurality of positions with respect to a first plurality of time instances.

In various embodiments, in relation to steps 102 and 104, an ultrasound transducer configured to emit ultrasound waves with respect to a plane (e.g., a cross-sectional plane perpendicular to the scanning direction) of a tissue volume and acquire the ultrasound waves reflected from such a plane of the tissue volume may be used to acquire the first and second series of ultrasound waves (in time series) at the first plurality of positions along the first scanning direction and the second plurality of positions along the second scanning direction of the tissue volume. Such an ultrasound transducer may be referred to as a 2D ultrasound transducer.

Various embodiments of the present invention are directed to cross-referencing 2D ultrasound scans or sweeps obtained through a freehand ultrasound scanning of the tissue volume. In this regard, a 2D ultrasound transducer (or a portable handheld ultrasound probe comprising a 2D ultrasound transducer) may be moved by an operator along a scanning direction of the tissue volume (e.g., across a length of the tissue volume along an axis) so as to perform ultrasound scanning of the tissue volume whereby a series of ultrasound waves are acquired by the 2D ultrasound transducer at a plurality of positions, respectively, along the scanning direction with respect to a plurality of time instances. The ultrasound waves received at each time instance (at the corresponding position) may then be processed to generate a 2D ultrasound image having associated therewith the corresponding position in a manner known in the art and thus need not be described herein in detail. Accordingly, a series of 2D ultrasound images of the tissue volume may be acquired, each 2D ultrasound image having an associated position (e.g., tagged or labelled with an associated position information), for example, corresponding to the position of the 2D ultrasound transducer at which the ultrasound waves (based on which the 2D ultrasound image is generated) were acquired or corresponding to the position/location along the tissue volume at which the ultrasound waves acquired by 2D ultrasound transducer were reflected from.

The 2D ultrasound transducer may be any conventional 2D ultrasound transducer configured to emit and acquire ultrasound waves with respect to a plane of a tissue volume and thus need not be described herein in detail. For example, and without limitation, a conventional 2D ultrasound transducer may comprise an array of transducer elements configured to emit and acquire ultrasound waves with respect to a plane of a tissue volume. Therefore, it will be appreciated by a person skilled in the art that the present invention is not limited to any particular type of 2D ultrasound transducer.

The method 100 further comprises a step 106 of generating a first 2D representation of the target anatomy from the first series of 2D ultrasound images, the first 2D representation associated with one of the images of the first series of 2D ultrasound images.

The method 100 further comprises a step 108 of generating a first simulated 2D representation of the target anatomy from the second series of 2D ultrasound images, the first simulated 2D representation and the first 2D representation of the target anatomy corresponding to one another in terms of viewing direction onto the target anatomy.

The method 100 further comprises a step 110 of processing the first 2D representation and the first simulated 2D representation of the target anatomy so as to at least substantially match pixel positions associated with the target anatomy in the first simulated 2D representation with pixel positions associated with the target anatomy in the first 2D representation. In various embodiments, the term "at least substantially matching" as used herein in connection with pixel positions in two different 2D entities (e.g., first 2D representation and first simulated 2D representation after processing) may be understood to mean that a position (e.g., 2D coordinates) of a pixel (or a plurality of pixels, e.g. all pixels) in one of the two 2D entities (e.g., first simulated 2D representation after processing) matches a position (e.g., 2D coordinates) of a corresponding pixel (or a plurality of corresponding pixels) in the other of the two 2D entities (e.g., first 2D representation after processing), or almost matches the position of the corresponding pixel (or the plurality of corresponding pixels), for example having a position deviation (e.g., between x coordinates and/or between y coordinates) that is less than or equal to a given number of pixel spacings, e.g. less than or equal to 10 pixel spacings, e.g. less than or equal to 5 pixel spacings, e.g. less than or equal to 2 pixel spacings, e.g. less than or equal to 1 pixel spacing.

The method 100 further comprises a step 112 of determining a first correspondence transformation matrix from the processed first 2D representation and the processed first simulated 2D representation of the target anatomy.

The method 100 further comprises a step 114 of generating a second 2D representation of the target anatomy from the second series of 2D ultrasound images, the second 2D representation associated with one of the images of the second series of 2D ultrasound images.

The method 100 further comprises a step 116 of generating a second simulated 2D representation of the target anatomy from the first series of 2D ultrasound images, the second simulated 2D representation and the second 2D representation of the target anatomy corresponding to one another in terms of viewing direction onto the target anatomy.

The method 100 further comprises a step 118 of processing the second 2D representation and the second simulated 2D representation of the target anatomy so as to at least substantially match pixel positions associated with the target anatomy in the second simulated 2D representation with pixel positions associated with the target anatomy in the second 2D representation.

The method 100 further comprises a step 120 of determining a second correspondence transformation matrix from the processed second 2D representation and the processed second simulated 2D representation of the target anatomy.

The method 100 further comprises a step 122 of using the first correspondence transformation matrix and the second correspondence transformation matrix to determine for a first location associated with the target anatomy in the second series of 2D ultrasound images a corresponding second location associated with the target anatomy in the first series of 2D ultrasound images. In various embodiments, the first location may be a point selected by a user on one of the images (image frames) of the second series of 2D ultrasound images, and the second location may be a (cross-referenced) point on one of the images (image frames) of the first series of 2D ultrasound images, obtained with the aid of the first and second transformation matrices.

In various embodiments, in relation to step 122, using the first correspondence transformation matrix and the second correspondence transformation matrix to determine the second location comprises applying a first function of the first correspondence transformation matrix and second correspondence transformation matrix to pixel coordinates corresponding to the first location so as to obtain pixel coordinates corresponding to the second location.

In various embodiments, the method 100 may further comprise: using the first correspondence transformation matrix and the second correspondence transformation matrix to determine for a third location associated with the target anatomy in the first series of 2D ultrasound images a corresponding fourth location associated with the target anatomy in the second series of 2D ultrasound images. In various embodiments, the third location may be a point selected by a user on one of the images (image frames) of the first series of 2D ultrasound images, and the fourth location may be a (cross-referenced) point on one of the images (image frames) of the second series of 2D ultrasound images, obtained with the aid of the first and second transformation matrices.

In various embodiments, using the first correspondence transformation matrix and the second correspondence transformation matrix to determine the fourth location comprises: applying a second function of the first correspondence transformation matrix and second correspondence transformation matrix to pixel coordinates corresponding to the third location so as to obtain pixel coordinates corresponding to the fourth location.

In various embodiments, the method 100 may further comprise: generating a first plurality of binary segmentation masks from the first series of 2D ultrasound images, each binary segmentation mask of the first plurality of binary segmentation masks corresponding to a respective one of the 2D ultrasound images of the first series of 2D ultrasound images. In various embodiments, the first 2D representation of the target anatomy may be generated from one of the binary segmentation masks of the first plurality of binary segmentation masks.

In various embodiments, the method 100 may further comprise generating a second plurality of binary segmentation masks from the second series of 2D ultrasound images, each binary segmentation mask of the second plurality of binary segmentation masks corresponding to a respective one of the 2D ultrasound images of the second series of 2D ultrasound images. In various embodiments, the second 2D representation of the target anatomy may be generated from one of the binary segmentation masks of the second plurality of binary segmentation masks.

In various embodiments, the first plurality of binary segmentation masks and/or the second plurality of binary segmentation masks may be obtained with the use of a segmentation method or process, which is known as such in the art of digital image processing. One example of a suitable segmentation method that may be used in accordance with various embodiments is the so-called U-Net, which is a convolutional neural network developed for biomedical image segmentation. In digital image processing and computer vision, image segmentation refers to the process of partitioning a digital image into multiple segments (sets of pixels, also known as image objects). More specifically, image segmentation refers to the process of assigning a label (or value) to every pixel in an image such that pixels with the same label (or value) share certain characteristics.

In various embodiments, in each binary segmentation mask, values of pixels associated with the target anatomy may assume a first value (e.g., "1"), while values of pixels not associated with the target anatomy may assume a second value (e.g., "0") that is different from the first value.

In various embodiments, the first 2D representation of the target anatomy may correspond to a largest binary segmentation mask among the first plurality of binary segmentation masks.

In various embodiments, the second 2D representation of the target anatomy may correspond to a largest binary segmentation mask among the second plurality of binary segmentation masks.

In various embodiments, the term "largest binary segmentation mask" as used herein may be understood to mean a binary segmentation mask, which has the largest number of pixels associated with the target anatomy, among a plurality of binary segmentation masks. For example, the largest binary segmentation mask may be the binary segmentation mask having the largest number of pixels having the first value (e.g., "1"), among the plurality of binary segmentation masks.

In various embodiments, in relation to step 106, generating the first 2D representation comprises removing regions in the largest binary segmentation mask among the first plurality of binary segmentation masks that are wrongly marked as corresponding to the target anatomy. For example, a largest continuous component searching algorithm may be applied to determine the largest continuous component (largest cluster) in the largest binary segmentation mask, and regions that are not connected to the largest continuous component may be removed from the mask.

In various embodiments, in relation to step 114, generating the second 2D representation comprises removing regions in the largest binary segmentation mask among the second plurality of binary segmentation masks that are wrongly marked as corresponding to the target anatomy. For example, a largest continuous component searching algorithm may be applied to determine the largest continuous component (largest cluster) in the largest binary segmentation mask, and regions that are not connected to the largest continuous component may be removed from the mask.

In various embodiments, in relation to step 108, generating the first simulated 2D representation of the target anatomy from the second series of 2D ultrasound images comprises generating the first simulated 2D representation of the target anatomy from the second plurality of binary segmentation masks. In various embodiments, regions in the first simulated 2D representation that are wrongly marked as corresponding to the target anatomy may be removed. For example, a largest continuous component searching algorithm may be applied to determine the largest continuous component (largest cluster), and regions that are not connected to the largest continuous component may be removed.

In various embodiments, in relation to step 116, generating the second simulated 2D representation of the target anatomy from the first series of 2D ultrasound images comprises generating the second simulated 2D representation of the target anatomy from the first plurality of binary segmentation masks. In various embodiments, regions in the second simulated 2D representation that are wrongly marked as corresponding to the target anatomy may be removed. For example, a largest continuous component searching algorithm may be applied to determine the largest continuous component (largest cluster), and regions that are not connected to the largest continuous component may be removed.

In various embodiments, in relation to step 110, processing the first 2D representation comprises generating a first signed distance map from the first 2D representation. In various embodiments, generating the first signed distance map comprises determining a boundary contour of the first 2D representation (e.g., of the largest binary segmentation mask among the first plurality of binary segmentation masks), generating a first distance map, in which the value of each pixel is the distance from the pixel to its closest contour pixel, converting the first 2D representation (e.g., the largest binary segmentation mask) to a first signed map, and generating the first signed distance map by element-wise multiplication of the first signed map and the first distance map.

In various embodiments, in relation to step 118, processing the second 2D representation comprises generating a second signed distance map from the second 2D representation. In various embodiments, generating the second signed distance map comprises determining a boundary contour of the 2D representation (e.g., of the largest binary segmentation mask among the second plurality of binary segmentation masks), generating a second distance map, in which the value of each pixel is the distance from the pixel to its closest contour pixel, converting the 2D representation (e.g., the largest binary segmentation mask) to a second signed map, and generating the second signed distance map by element-wise multiplication of the second signed map and the second distance map.

In various embodiments, in relation to step 110, processing the first simulated 2D representation comprises scaling a width of the first simulated 2D representation so as to match a width of the first 2D representation.

In various embodiments, in relation to step 118, processing the second simulated 2D representation comprises scaling a width of the second simulated 2D representation so as to match a width of the second 2D representation.

In various embodiments, in relation to step 110, processing the first simulated 2D representation further comprises determining and sampling contour pixels associated with a contour of the target anatomy from the scaled first simulated 2D representation.

In various embodiments, in relation to step 118, processing the second simulated 2D representation further comprises determining and sampling contour pixels associated with a contour of the target anatomy from the scaled second simulated 2D representation.

In various embodiments, in relation to step 110, processing the first simulated 2D representation further comprises sampling a first subset of pixels from the scaled first simulated 2D representation.

In various embodiments, in relation to step 118, processing the second simulated 2D representation further comprises sampling a second subset of pixels from the scaled second simulated 2D representation.

In various embodiments, in relation to step 110, processing the first simulated 2D representation further comprises estimating coarse shifts between the scaled first simulated 2D representation and the first 2D representation using the first signed distance map and the first sampled subset of pixels.

In various embodiments, in relation to step 118, processing the second simulated 2D representation further comprises estimating coarse shifts between the scaled second simulated 2D representation and the second 2D representation using the second signed distance map and the sampled second subset of pixels.

In various embodiments, in relation to step 112, determining the first correspondence transformation matrix comprises estimating a scale and translation between the scaled first simulated 2D representation and the first 2D representation by minimizing a first alignment cost defined as a first cost function with respect to the first correspondence transformation matrix. In various embodiments, the first alignment cost is defined as a sum of square distance with respect to the first correspondence transformation matrix.

In various embodiments, in relation to step 120, determining the second correspondence transformation matrix comprises estimating a scale and translation between the scaled second simulated 2D representation and the second 2D representation by minimizing a second alignment cost defined as a second cost function with respect to the second correspondence transformation matrix. In various embodiments, the second alignment cost is defined as a sum of square distance with respect to the second correspondence transformation matrix In various embodiments, minimizing the first alignment cost and/or minimizing the second alignment cost comprises applying an optimization algorithm, for example the Gauss-Newton algorithm.

In various embodiments, the first scanning direction corresponds to a transverse scan of the tissue volume and the second scanning direction corresponds to a sagittal scan of the tissue volume.

In various embodiments, the target anatomy comprises at least one of: a body organ, a portion of a body organ (e.g., thyroid lobe), a portion of a vascular system.

In various embodiments, the body organ comprises at least one of: thyroid, prostate, bladder, heart, lung(s), stomach, liver, kidney(s).

FIG. 2 depicts a schematic block diagram of a system 200 for cross-referencing of two-dimensional (2D) ultrasound scans of a tissue volume according to various embodiments of the present invention, such as corresponding to the method 100 for cross-referencing of two-dimensional (2D) ultrasound scans of a tissue volume using at least one processor as described hereinbefore, according to various embodiments of the present invention.

The system 200 comprises a memory 204, and at least one processor 206 communicatively coupled to the memory 204, and configured to: generate a first series of 2D ultrasound images of a tissue volume associated with a first plurality of positions, respectively, along a first scanning direction of the tissue volume, the tissue volume including a target anatomy; generate a second series of 2D ultrasound images of the tissue volume associated with a second plurality of positions, respectively, along a second scanning direction of the tissue volume, wherein the second scanning direction is at least substantially orthogonal to the first scanning direction; generate a first 2D representation of the target anatomy from the first series of 2D ultrasound images, the first 2D representation associated with one of the images of the first series of 2D ultrasound images; generate a first simulated 2D representation of the target anatomy from the second series of 2D ultrasound images, the first simulated 2D representation and the first 2D representation of the target anatomy corresponding to one another in terms of viewing direction onto the target anatomy; process the first 2D representation and the first simulated 2D representation of the target anatomy so as to at least substantially match pixel positions associated with the target anatomy in the first simulated 2D representation with pixel positions associated with the target anatomy in the first 2D representation; determine a first correspondence transformation matrix from the processed first 2D representation and the processed first simulated 2D representation of the target anatomy; generate a second 2D representation of the target anatomy from the second series of 2D ultrasound images, the second 2D representation associated with one of the images of the second series of 2D ultrasound images; generate a second simulated 2D representation of the target anatomy from the first series of 2D ultrasound images, the second simulated 2D representation and the second 2D representation of the target anatomy corresponding to one another in terms of viewing direction onto the target anatomy; process the second 2D representation and the second simulated 2D representation of the target anatomy so as to at least substantially match pixel positions associated with the target anatomy in the second simulated 2D representation with pixel positions associated with the target anatomy in the second 2D representation; determine a second correspondence transformation matrix from the processed second 2D representation and the processed second simulated 2D representation of the target anatomy; and use the first correspondence transformation matrix and the second correspondence transformation matrix to determine for a first location associated with the target anatomy in the second series of 2D ultrasound images a corresponding second location associated with the target anatomy in the first series of 2D ultrasound images.

It will be appreciated by a person skilled in the art that the at least one processor 206 may be configured to perform the required functions or operations through set(s) of instructions (e.g., software modules) executable by the at least one processor 206 to perform the required functions or operations.

Accordingly, as shown in FIG. 2, the system 200 may further comprise a 2D ultrasound image generator 208 configured to generate the first series of 2D ultrasound images and the second series of 2D ultrasound images; a 2D representation generator 210 configured to generate the first 2D representation of the target anatomy from the first series of 2D ultrasound images, and generate the second 2D representation of the target anatomy from the second series of 2D ultrasound images; a simulated 2D representation generator 212 configured to generate the first simulated 2D representation of the target anatomy from the second series of 2D ultrasound images, and generate the second 2D representation of the target anatomy from the second series of 2D ultrasound images; a 2D and simulated 2D representation processor 214 configured to process the first 2D representation and the first simulated 2D representation of the target anatomy, and process the second 2D representation and the second simulated 2D representation of the target anatomy; a correspondence transformation matrix determiner 216 configured to determine the first correspondence transformation matrix from the processed first 2D and first simulated 2D representations, and determine the second correspondence transformation matrix from the processed second 2D and second simulated 2D representations; and a corresponding location determiner 218 configured to determine for a first location associated with the target anatomy in the second series of 2D ultrasound images a corresponding second location associated with the target anatomy in the first series of 2D ultrasound images, by using the first correspondence transformation matrix and the second correspondence transformation matrix.

In some embodiments, the system 200 may further optionally comprise an ultrasound transducer 202 communicatively coupled to the memory 204 and the at least one processor 206. In some embodiments, the ultrasound transducer 202 may be installed in a freehand ultrasound probe.

In some embodiments, the ultrasound image generator 208 may be configured to generate the first series of 2D ultrasound images based on a first series of ultrasound waves acquired by the ultrasound transducer 202 positioned at the first plurality of positions with respect to a first plurality of time instances; and generate the second series of 2D ultrasound images based on a second series of ultrasound waves acquired by the ultrasound transducer 202 positioned at the second plurality of positions with respect to a second plurality of time instances.

Alternatively, or in addition, in some embodiments, the memory 204 may be configured to store first image data related to a first series of ultrasound waves acquired by an ultrasound transducer (e.g., ultrasound transducer 202) positioned at the first plurality of positions with respect to a first plurality of time instances; and store second image data related to a second series of ultrasound waves acquired by the ultrasound transducer (e.g., ultrasound transducer 202) positioned at the second plurality of positions with respect to a second plurality of time instances; and the at least one processor 206 (e.g., the 2D ultrasound image generator 208) may be configured to: generate the first series of 2D ultrasound images based on the first image data stored in the memory 204; and generate the second series of 2D ultrasound images based on the second image data stored in the memory 204.

It will be appreciated by a person skilled in the art that the above-mentioned modules are not necessarily separate modules, and one or more modules may be realized by or implemented as one functional module (e.g., a circuit or a software program) as desired or as appropriate without deviating from the scope of the present invention. For example, the 2D ultrasound image generator 208, the 2D representation generator 210, the simulated 2D representation generator 212, the 2D and simulated 2D representation processor 214, the correspondence transformation matrix determiner 216, and/or the corresponding location determiner 218 may be realized (e.g., compiled together) as one executable software program (e.g., software application or simply referred to as an "app"), which for example may be stored in the memory 204 and executable by the at least one processor 206 to perform the functions/operations as described herein according to various embodiments.

In various embodiments, the system 200 corresponds to the method 100 as described hereinbefore with reference to FIG. 1, therefore, various functions or operations configured to be performed by the least one processor 206 may correspond to various steps of the method 100 described hereinbefore according to various embodiments, and thus need not be repeated with respect to the system 200 for clarity and conciseness. In other words, various embodiments described herein in context of the methods are analogously valid for the respective systems or devices, and vice versa.

For example, in various embodiments, the memory 204 may have stored therein the 2D ultrasound image generator 208, the 2D representation generator 210, the simulated 2D representation generator 212, the 2D and simulated 2D representation processor 214, the correspondence transformation matrix determiner 216, and/or the corresponding location determiner 218, which respectively correspond to various steps of the method 100 as described hereinbefore, which are executable by the at least one processor 206 to perform the corresponding functions/operations as described herein.

A computing system, a controller, a microcontroller or any other system providing a processing capability may be provided according to various embodiments in the present disclosure. Such a system may be taken to include one or more processors and one or more computer-readable storage mediums. For example, the system 200 described hereinbefore may include a processor (or controller) 206 and a computer-readable storage medium (or memory) 204 which are for example used in various processing carried out therein as described herein. A memory or computer-readable storage medium used in various embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In various embodiments, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g., a microprocessor (e.g., a Complex Instruction Set Computer (CISC) processor or a Reduced Instruction Set Computer (RISC) processor). A "circuit" may also be a processor executing software, e.g., any kind of computer program, e.g., a computer program using a virtual machine code, e.g., Java. Any other kind of implementation of the respective functions which will be described in more detail below may also be understood as a "circuit" in accordance with various alternative embodiments. Similarly, a "module" may be a portion of a system according to various embodiments in the present invention and may encompass a "circuit" as above, or may be understood to be any kind of a logic-implementing entity therefrom.

Some portions of the present disclosure are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "generating", "estimating", "modifying", "rendering" or the like, refer to the actions and processes of a computer system, or similar electronic device, that manipulates and transforms data represented as physical quantities within the computer system into other data similarly represented as physical quantities within the computer system or other information storage, transmission or display devices.

The present specification also discloses a system, a device or an apparatus for performing the operations/functions of the methods described herein. Such a system, device or apparatus may be specially constructed for the required purposes, or may comprise a general purpose computer or other device selectively activated or reconfigured by a computer program stored in the computer. The algorithms presented herein are not inherently related to any particular computer or other apparatus. Various general-purpose machines may be used with computer programs in accordance with the teachings herein. Alternatively, the construction of more specialized apparatus to perform the required method steps may be appropriate.

In addition, the present specification also at least implicitly discloses a computer program or software/functional module, in that it would be apparent to the person skilled in the art that the individual steps of the methods described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the scope of the invention. It will be appreciated by a person skilled in the art that various modules described herein (e.g., the 2D ultrasound image generator 208, the 2D representation generator 210, the simulated 2D representation generator 212, the 2D and simulated 2D representation processor 214, the correspondence transformation matrix determiner 216, and/or the corresponding location determiner 218) may be software module(s) realized by computer program(s) or set(s) of instructions executable by a computer processor to perform the required functions, or may be hardware module(s) being functional hardware unit(s) designed to perform the required functions. It will also be appreciated that a combination of hardware and software modules may be implemented.

Furthermore, one or more of the steps of a computer program/module or method described herein may be performed in parallel rather than sequentially. Such a computer program may be stored on any computer readable medium.

The computer readable medium may include storage devices such as magnetic or optical disks, memory chips, or other storage devices suitable for interfacing with a general-purpose computer. The computer program when loaded and executed on such a general-purpose computer effectively results in an apparatus that implements the steps of the methods described herein.

In various embodiments, there is provided a computer program product, embodied in one or more computer-readable storage mediums (non-transitory computer-readable storage medium), comprising instructions (e.g., the 2D ultrasound image generator 208, the 2D representation generator 210, the simulated 2D representation generator 212, the 2D and simulated 2D representation processor 214, the correspondence transformation matrix determiner 216, and/or the corresponding location determiner 218) executable by one or more computer processors to perform a method 100 for cross-referencing of two-dimensional (2D) ultrasound scans of a tissue volume as described hereinbefore with reference to FIG. 1. Accordingly, various computer programs or modules described herein may be stored in a computer program product receivable by a system (e.g., a computer system or an electronic device) therein, such as the system 200 as shown in FIG. 2, for execution by at least one processor 206 of the system 200 to perform the required or desired functions.

The software or functional modules described herein may also be implemented as hardware modules. More particularly, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the software or functional module(s) described herein can also be implemented as a combination of hardware and software modules.

It will be appreciated by a person skilled in the art that the system 200 may be made up of separate units or as one integrated unit. For example, in various embodiments, the system 200 may comprise a computer system including the at least one processor 206, the memory 204, the 2D ultrasound image generator 208, the 2D representation generator 210, the simulated 2D representation generator 212, the 2D and simulated 2D representation processor 214, the correspondence transformation matrix determiner 216, and the corresponding location determiner 218, and a separate ultrasound probe including the ultrasound transducer 202 communicatively coupled to the computer system. In other words, the separate ultrasound probe may acquire a series of ultrasound waves with respect to a tissue volume, and the series of ultrasound waves may then be transmitted (e.g., based on wireless or wired communication) to the computer system at a different location for performing the method for cross-referencing of two-dimensional (2D) ultrasound scans of a tissue volume as described hereinbefore with reference to FIG. 1. In various other embodiments, the system 200 may correspond to, or may be embodied as, an ultrasound probe, including the ultrasound transducer 202, the at least one processor 206, the memory 204, the 2D ultrasound image generator 208, the 2D representation generator 210, the simulated 2D representation generator 212, the 2D and simulated 2D representation processor 214, the correspondence transformation matrix determiner 216, and the corresponding location determiner 218.

Figure 3:
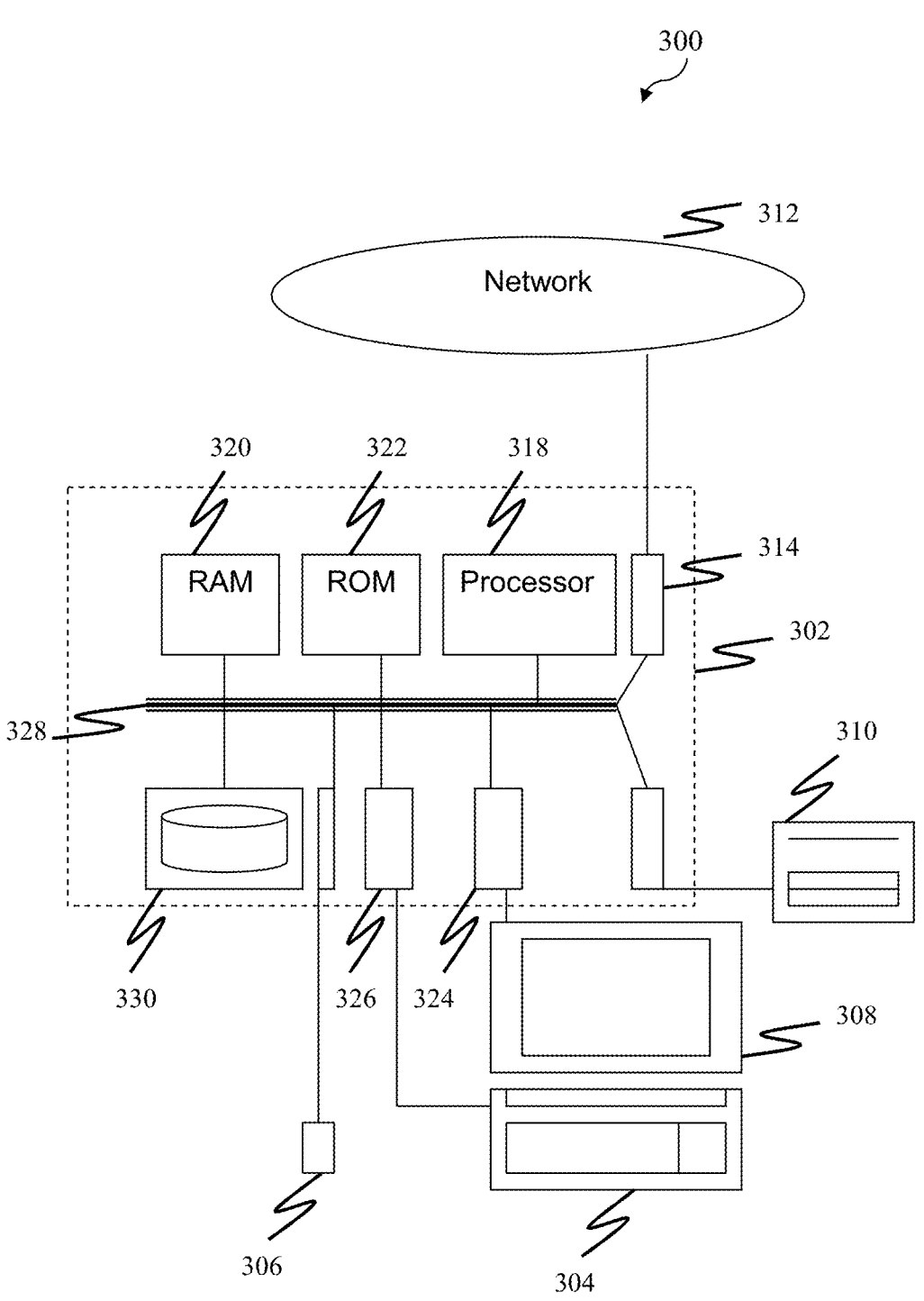
FIG. 3 depicts a schematic block diagram of an exemplary computer system which may be used to realize or implement the system for cross-referencing of 2D ultrasound scans of a tissue volume according to various embodiments of the present invention, such as the system as depicted in FIG. 2.
Figure 4B:
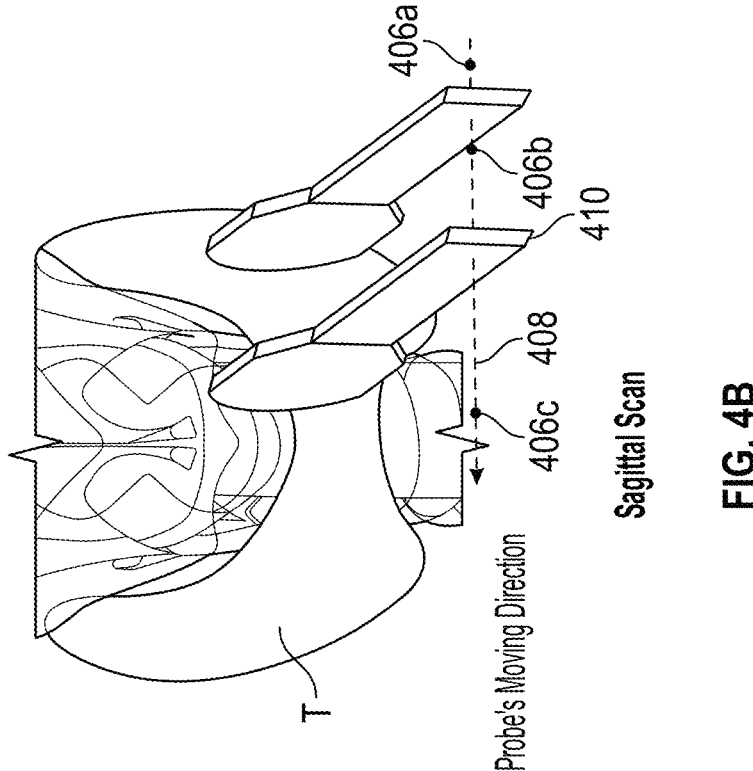
FIG. 4 depicts a schematic illustration of the human thyroid as well as sample transverse and sagittal thyroid ultrasound sweep images
Figure 4A:
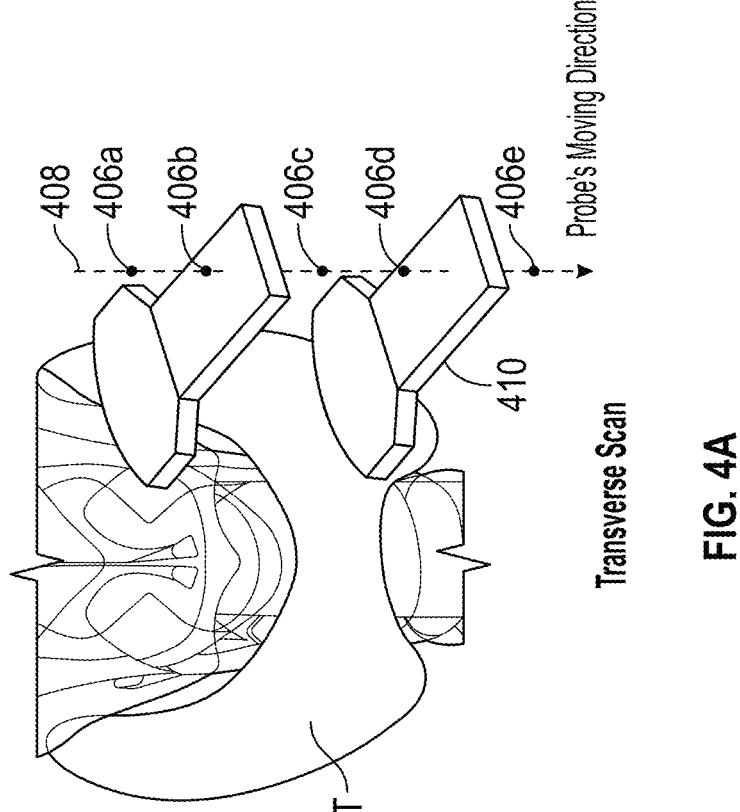
Figure 4D:
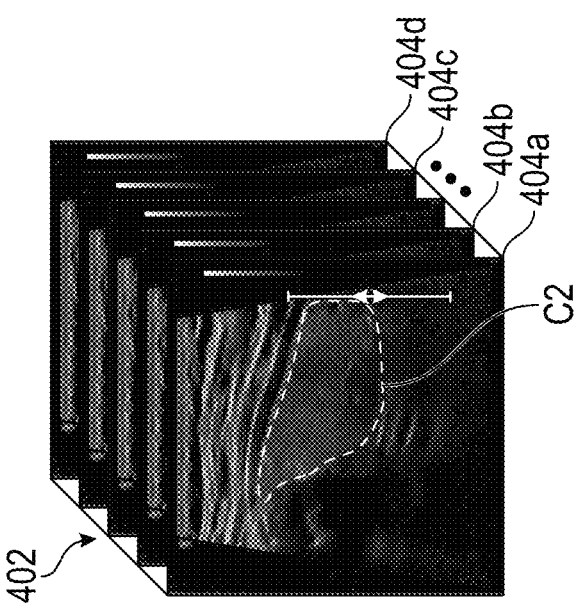
Figure 4C:
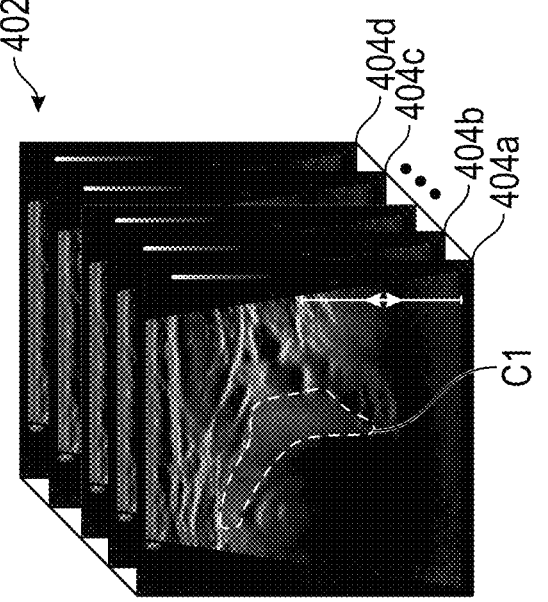

In various embodiments, the above-mentioned computer system may be realized by any computer system (e.g., portable or desktop computer system), such as a computer system 300 as schematically shown in FIG. 3 as an example only and without limitation. Various methods/steps or functional modules (e.g., the 2D ultrasound image generator 208, the 2D representation generator 210, the simulated 2D representation generator 212, the 2D and simulated 2D representation processor 214, the correspondence transformation matrix determiner 216, and/or the corresponding location determiner 218) may be implemented as software, such as a computer program being executed within the computer system 300, and instructing the computer system 300 (in particular, one or more processors therein) to conduct the methods/functions of various embodiments described herein. The computer system 300 may comprise a computer module 302, input modules, such as a keyboard 304 and a mouse 306, and a plurality of output devices such as a display 308, and a printer 310. The computer module 302 may be connected to a computer network 312 via a suitable transceiver device 314, to enable access to e.g., the Internet or other network systems such as Local Area Network (LAN) or Wide Area Network (WAN). The computer module 302 in the example may include a processor 318 for executing various instructions, a Random Access Memory (RAM) 320 and a Read Only Memory (ROM) 322. The computer module 302 may also include a number of Input/Output (I/O) interfaces, for example I/O interface 324 to the display 308, and I/O interface 326 to the keyboard 304. The components of the computer module 302 typically communicate via an interconnected bus 328 and in a manner known to the person skilled in the relevant art.

It will be appreciated by a person skilled in the art that the terminology used herein is for the purpose of describing various embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

For illustration purpose only and without limitation, FIG. 4 depicts example sweeps (or series or sequence or plurality) 402 of 2D ultrasound images (e.g., 404a, 404b, 404c, and 404d) of a tissue volume associated with a plurality of positions along a scanning direction 408 of the tissue volume. In this regard, the series 402 of 2D ultrasound images may be generated based on a series of ultrasound waves acquired by an ultrasound transducer (e.g., installed in an ultrasound probe 410) at the plurality of positions (e.g., 406a, 406b, 406c, 406d, 406e) along the ultrasound probe's scanning direction 408.

In order that the present invention may be readily understood and put into practical effect, various example embodiments of the present invention will be described hereinafter by way of examples only and not limitations. It will be appreciated by a person skilled in the art that the present invention may, however, be embodied in various different forms or configurations and should not be construed as limited to the example embodiments set forth hereinafter. Rather, these example embodiments are provided so that this disclosure will be thorough and complete, and will fully convey the scope of the present invention to those skilled in the art.

Various embodiments of the present invention disclose a method and a system that are able to assist a user by automatically cross-referencing the points in two different views (e.g., TRX and SAG views) using the information common in the two perpendicular ultrasound sweeps. More specifically, various embodiments of this invention may assist the user with locating the corresponding region of interest on the second view (e.g., sagittal view), when the user selects a region of interest on the first view (e.g., transverse view).

In accordance with various embodiments, for the cross-referencing, two 2D sweep scans of a 3D anatomy from two (almost) orthogonal views may be provided. Without loss of generality and for the sake of simplicity, hereafter it will be mainly assumed that the first sweep is taken from the transverse (TRX) view while the second sweep is from the sagittal (SAG) view.

In accordance with various embodiments, a segmentation method may be applied to segment the boundary of a target anatomy (e.g., thyroid gland) in each 2D frame in both views. In various embodiments, the term "target anatomy" as used herein may refer to an anatomy (or, internal anatomical structure) of interest, such as, for example, a body organ (e.g., thyroid, prostate, bladder, heart, lung(s), stomach, liver, kidney(s), or other body organ) or a portion of the vascular system (e.g., carotid artery).

Since both views contain the same 3D anatomy, there is common information in the set of two perpendicular ultrasound sweeps. In accordance with various embodiments, this common information is used to compute a transformation matrix that maps any given point on the TRX view, $[idx_{trx}, y_{trx}, x_{trx}]$, to the corresponding point on the SAG view, $[idx_{sag}, y_{sag}, x_{sag}]$. Here, idx denotes the frame index, and x and y denote the coordinates of the respective point. The frame index denotes the particular image frame of the series of 2D ultrasound images (sweep), in which the respective point is located. For example, $[idx_{trx}, y_{trx}, x_{trx}]$ denotes a point that is located in a TRX frame (a frame of the TRX sweep) with index $idx_{trx}$ and that has coordinates $y_{trx}, x_{trx}$ within that frame.

In accordance with various embodiments of the present invention, a (computer-implemented) method or algorithm for computation of a transformation for a cross-referencing tool or system may be provided. The cross-referencing tool or system may assist a user with locating on a second image plane (e.g., sagittal plane) an approximate region for a region of interest (ROI) or landmark (e.g., a nodule), when the region of interest or landmark (e.g., nodule) has been identified before (e.g., by the user) on a first image plane (e.g., transverse plane).

In accordance with various embodiments, the cross-referencing tool or system may use a linear transformation (matrix) to select a particular frame index and coordinates within a sagittal (longitudinal) image, based on a frame index and coordinates provided by the user on a transverse image. The mapping obtained from transformations may be used to place a transverse-image and sagittal-image pair into the same spatial coordinate system, allowing transverse-view points to be mapped to sagittal-view points.

When invoked by the user, the method or algorithm may take in images of two 2D ultrasound scans (e.g., series of 2D thyroid images) carried out along orthogonal scanning directions, e.g., a transverse (TRX) Sweep (including a plurality of TRX images (image frames)) and a sagittal (SAG) Sweep (including a plurality of SAG images (image frames), as input, and may output a pair of transformation matrices (herein also referred to as correspondence transformation matrices) $T_{trx}$ and $T_{sag}$.

In the following, aspects of computation of a pair of transformation matrices $T_{trx}$ and $T_{sag}$ will be described in the context of 2D ultrasound imaging of a thyroid lobe including a transverse (TRX) sweep and a sagittal (SAG) sweep, as an illustrative example. The thyroid lobe may be an example of a target anatomy.

In accordance with some embodiments, the computation of the transformation matrices may include the following steps:

1. Segment the target anatomy (thyroid lobe) in every frame for both the TRX sweep and the SAG sweep to obtain binary masks (also referred to as binary segmentation masks) for the image frames of the TRX sweep and the SAG sweep. In the binary masks, pixel values assume either a first value (e.g., "1"), signaling thyroid region, or a second value (e.g., "0"), signaling non-thyroid region. The segmentation can be carried out by any generic segmentation method (e.g. classical or neural-network based segmentation method), which may be known as such in the art.

2. Find the optimal binary mask from the TRX sweep and find the optimal binary mask from the SAG sweep. The optimal binary mask for the TRX sweep may be the largest binary mask among the binary masks obtained from the TRX sweep, and the optimal binary mask for the SAG sweep may be the largest binary mask among the binary masks obtained from the SAG sweep. The optimal (or largest) binary mask for the TRX sweep may be referred to as first 2D representation of the thyroid lobe (target anatomy), and the optimal (or largest) binary mask for the SAG sweep may be referred to as second 2D representation of the thyroid lobe (target anatomy).

3. Reshape (projection) the full stack of masks for the SAG sweep from $(H_{sag} \times W_{sag} \times N_{sag})$ to $(H_{sag} \times N_{sag} \times W_{sag})$, where $N_{sag}$ is the number of image frames in the SAG sweep and $H_{sag}$ and $W_{sag}$ are the number of rows and columns of each SAG image frame, respectively. By doing this, a simulated stack of TRX masks is created from the original SAG stack. Then, the largest simulated TRX mask is selected, in a similar manner as in step 2.

4. Find an initial (coarse) width to height ratio for the simulated TRX frame. This ratio matches the simulated TRX and actual TRX images, and may later be optimized to refine this ratio. In various embodiments, the width to height ratio may be used to scale the width of the simulated TRX mask so as to obtain a scaled version of the simulated TRX mask, which may be referred to as scaled first simulated 2D representation of the thyroid lobe (target anatomy).

5. Create a distance map for the selected TRX mask (i.e., for the optimal binary mask for the TRX sweep obtained in step 2). In the distance map (also referred to as TRX distance map), a pixel's value is the distance from that pixel to the nearest pixel on the edge of the thyroid lobe (target anatomy) in the TRX mask. Points from within the thyroid lobe from the simulated TRX mask may be sampled to be used in the next step, since using all the pixels inside the thyroid lobe (target anatomy) may be computationally intensive.

6. Use a vectorized heuristic search method to solve the optimization problem that would align the previously generated images (the TRX distance map and the points sampled from the simulated TRX mask).

7. Sample points from the edge of the thyroid lobe (target anatomy) mask in the simulated TRX mask and use the alignment parameters found in the previous step and an optimization algorithm, such as the Gauss-Newton algorithm, to minimize the alignment cost and find the transformation matrix $T_{trx}$.

8. Repeat steps (3) to (7) above from masks of TRX sweep and compute the transformation matrix $T_{sag}$.

9. Optional: Find the in-plane shift for every frame, which is done similar to step 6 and results in finding a matrix $RC_{trx}$, to compensate for the hand movement (of the user, e.g., clinician) present during the scanning procedure (using a freehand ultrasound probe).

10. Having $T_{trx}$ and $T_{sag}$ (and optionally $RC_{trx}$), any point from the TRX sweep (having frame index $idx_{trx}$ and coordinates $(x_{trx}, y_{trx})$) may be mapped to a corresponding point on the SAG sweep (having frame index $idx_{sag}$ and coordinates $(x_{sag}, y_{sag})$). Thus, cross-referencing between the images of the TRX and SAG sweeps may be achieved. In other words, for any point in transverse view, i.e. $(x_{trx}, y_{trx})$ at frame index $idx_{trx}$, the cross-referenced point in sagittal view, i.e. $(x_{sag}, y_{sag})$ at frame index $idx_{sag}$ may be obtained. The frame index denotes the particular frame (2D ultrasound image frame) in the series of 2D ultrasound images (images frames) from the TRX sweep or SAG sweep.

In the following, a flow diagram 500 illustrating aspects of a method for cross-referencing 2D ultrasound scans in accordance with various embodiments (for example, the method 100 shown in FIG. 1), will be described with reference to FIG. 5.

Figure 5:
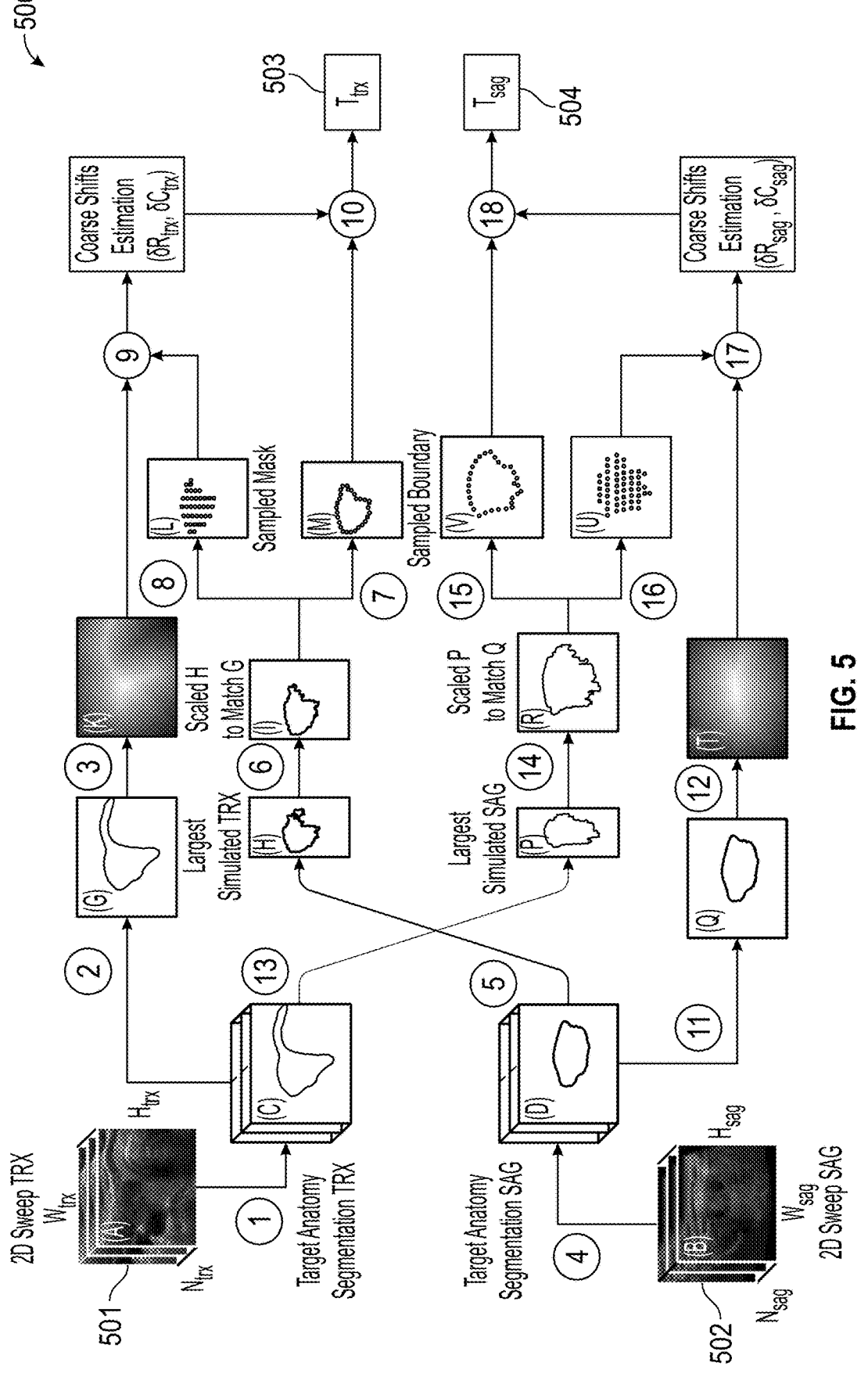
FIG. 5 depicts a flow diagram illustrating aspects of a method for cross-referencing of 2D ultrasound scans of a tissue volume according to various embodiments of the present invention.

In FIG. 5, a pair of TRX and SAG view freehand ultrasound sweeps may be provided as input. See, 501 and 502 on lefthand side in FIG. 5: (A) ("2D sweep TRX", i.e., transverse scan) and "(B)" ("2D sweep SAG", i.e., sagittal scan). This may be included in steps 102 and 104 in the method of FIG. 1. In an illustrative example, thyroid gland images may be captured by an ultrasound imaging device once from a first view (TRX plane) and then from a second view (SAG plane), for example similarly as shown and described with (a) and (b) of FIG. 4.

Furthermore, two transformation matrices $T_{sag}$ and $T_{trx}$ may be provided as output (see, 503 and 504 on righthand side in FIG. 5) that may be used to map any point $(x_{trx}, y_{trx})$ and frame index $idx_{trx}$ on the TRX sweep 501 to the corresponding point $(x_{sag}, y_{sag})$ and frame index $idx_{sag}$ in the SAG sweep 502, and vice versa. This may be included in steps 112, 120, and 122 in the method of FIG. 1.

The mapping (cross-referencing) may be expressed by the following equations (1) and (2):

$$(idx_{sag}, y_{sag}, x_{sag}) = f_{sag}(T_{trx}, T_{sag}, ws_{sag}, idx_{trx}, y_{trx}, x_{trx},) \tag{1}$$

$$(idx_{trx}, y_{trx}, x_{trx}) = f_{trx}(T_{trx}, T_{sag}, ws_{trx}, idx_{sag}, y_{sag}, x_{sag}) \tag{2}$$

Here $(idx_{trx}, y_{trx}, x_{trx})$ denotes a point in transverse (TRX) view, $(idx_{sag}, y_{sag}, x_{sag})$ denotes the corresponding (i.e., cross-referenced) point in sagittal (SAG) view, $T_{sag}$ and $T_{trx}$ are the correspondence transformation matrices, and $f_{sag}$ and $f_{trx}$ are mapping functions of the transformation matrices $T_{sag}$ and $T_{trx}$ and scaling factors $ws_{trx}$, $ws_{sag}$ that map the locations from TRX to SAG view and vice versa.

Methodology

The task underlying various embodiments of the present invention may be seen in matching the points of the 3D anatomy from two orthogonal (or substantially orthogonal) views, in particular TRX and SAG views as illustrated in the diagram 500 shown in FIG. 5. In accordance with various embodiments, the 3D pixel-to-pixel cross-referencing problem may be decomposed into two parallel co-registration problems that may be solved concurrently.

From TRX to SAG: Cross-Referencing of Points
on TRX View Sweep to the Corresponding Points
on SAG View Sweep (Upper Half of Diagram 500)

To use the common (shared) information in the two views, a "simulated version" of the target anatomy in a first view (view 1, hereafter TRX) may be reconstructed from the scans of a second view (view 2, hereafter SAG), and vice versa. The simulated view is obtained by projection of the first view (view 1) in the second view (view2).

After some post-processing on the simulated view, the simulated TRX and original TRX may be co-registered to compute the correspondence transformation matrix Tom.

Similarly, a simulated SAG may be generated from the 2D sweep in TRX, and the correspondence transformation matrix $T_{sag}$ may be computed.

Again with reference to the flow diagram 500 shown in FIG. 5, a more detailed explanation of aspects of the method will now be given. In the flow diagram 500, individual steps are indicated by arrows and associated numbers, such as ①, ②, ③, ④, . . . , etc. It should be understood, that the numbering does not necessarily imply a sequence in time, as, for example, some steps (for example, steps ① and ④) may be carried out sequentially or concurrently, and/or some steps labelled with a "higher" number (e.g., step ⑪) may also be carried out before or concurrently with a step labelled with a "lower" number (e.g., step ②). Furthermore, the arrows (steps) in the flow diagram 500 may generally indicate a transition between different stages of the process flow, each stage being represented by an image labelled with a capital letter, such as "A", "B", "C", etc.

The individual steps shown in the flow diagram 500 of FIG. 5 can be described as follows:

Step ①: Segmentation of target anatomy in the first view (TRX view): Feed each frame of the TRX view of the 2D sweep of the target anatomy, see (A) with image size of (height $H_{trx}$, width $W_{trx}$) and number of TRX frames $N_{trx}$, into a segmentation method (for example, U-Net segmentation network), to get the corresponding binary segmentation mask (C). The value of the pixels in the segmentation masks is either 1 (corresponds to thyroid region), or 0 (corresponds to non-thyroid region). For illustration, pixels in (C) corresponding to the target anatomy (thyroid region) are white, while pixels corresponding to non-thyroid region are black. Step ① may be included in step 106 of the method 100 shown in FIG. 1.

Step ②: Find the largest (optimal) TRX segmentation mask (G) among the generated masks (C) that represents the target anatomy. The term "optimal" here denotes the segmentation mask with the largest segmentation mask of the target anatomy. Step ② may be included in step 106 of the method 100 shown in FIG. 1.

Step ③: Generate the signed distance map (K) from segmentation mask (G). To obtain the signed distance map (K), first the boundary contour of segmentation mask (G) may be determined (i.e., the boundary contour of the target anatomy (thyroid region) in the segmentation mask (G)). The value of each pixel in the distance map is the distance from the pixel to its closest contour pixel. The values of the pixels in the distance map corresponding to the contour pixels are zero. To obtain the signed distance map, the thyroid segmentation mask (G) may be converted to a signed map (hereafter referred to as "signed (G)"), in which thyroid and non-thyroid pixels have values –1 and 1 rather than 0 and 1. The signed distance map (K) is then generated by element-wise multiplication of the signed (G) and the distance map. Step ③ may be included in step 110 of the method 100 shown in FIG. 1.

Step ④: Segmentation of target anatomy in the second view (SAG view): Feed the 2D sweep of SAG view, (B) with shape of ($H_{sag}$, $W_{sag}$, $N_{sag}$), into the SAG segmentation method to get the corresponding binary segmentation mask in the SAG view (D). Similar as in (C), pixels in (D) corresponding to the target anatomy (thyroid region) are white, while pixels corresponding to non-thyroid region are black. Step ④ may be included in step 114 of the method 100 shown in FIG. 1.

Step ⑤: Generate the simulated TRX segmentation and extract the largest simulated TRX segmentation mask (H) with shape of ($H_{sag}$, $N_{sag}$) from the generated SAG masks (D). Step ⑤ may be included in step 108 of the method 100 shown in FIG. 1.

Step ⑥: Estimate the coarse scale factor $ws_{trx}$ of the width ($N_{sag}$) of the simulated TRX mask (H). The coarse estimation is based on the fact that the width over height ratio (WoH) of the thyroid in the real TRX frame (G) and the simulated TRX frame (I) should be the same.

In ultrasound 2D sweeps, the in-plane pixel spacing (width and height) within a scanned frame is known while the out-of-plane pixel spacing between two consecutive frames is not known, which mainly depends on the moving direction and speed of the ultrasound probe. That means the height ($H_{sag}$) of the simulated TRX mask may be almost correct while the width ($N_{sag}$) may need to be scaled by a scale factor ($ws_{trx}$). The goal of this step is to estimate the coarse scale factor $ws_{trx}$ of the width ($N_{sag}$) of the simulated TRX mask (H). The coarse estimation is based on the fact that the width over height ratio (WoH) of the thyroid in the real TRX frame (G) and the simulated TRX frame (I) should be the same. Step ⑥ may be included in step 110 of the method 100 shown in FIG. 1.

Step ⑦: Extract and sample the contour pixels (M) from the simulated TRX segmentation mask (I). Given mask (I), its contours are extracted first and then the longest contour is kept. The obtained longest contour is a one pixel-width chain and its pixels' coordinates are ordered and stored in a matrix with shape of (2, num_pixels), where num_pixels denotes the number of pixels in the longest contour. Then a subset (e.g., 50) of the obtained num_pixels contour pixels may be sampled for further edge based alignment in step ⑩. In (M), the sampled contour pixels are shown as white dots. Step ⑦ may be included in step 110 of the method 100 shown in FIG. 1.

Step ⑧: Sample regional anchor pixels (L) from (I). Due to the large number of foreground pixels in (I), a subset of them is sampled. For example, the foreground pixels for which both row and column indices can be divided by a given number n (e.g., and without limitation, n=25) may be kept. In (L), the sampled pixels are shown as white dots (L). Step may be included in step 110 of the method 100 shown in FIG. 1.

Step ⑨: Estimate the coarse shifts ($\delta R_{trx}$, $\delta C_{trx}$) between the thyroid masks in (I) and (G) by maximizing the alignment response computed from (L) and (K), using following formula (3):

$$\arg\max_{\delta R, \delta C} \Sigma K((r+\delta R_{trx}, c+\delta C_{trx})|L(r, c)>0) \qquad (3)$$

where (r, c) are the row number and column number of foreground pixels in (L). Step ⑨ may be included in step 110 of the method 100 shown in FIG. 1.

Step ⑩: Estimate the scale and translation between the segmentation mask in (I) and that in (G) by minimizing the alignment cost defined as the sum of square distance with respect to the transformation matrix $T_{trx}$, using following formula (4):

$$\arg\min_{T_{trx}} \Sigma J(W((x|M(x)==1), T_{trx})) \qquad (4)$$

where J is the distance map (see FIG. 6) and W is the warping (transformation) of the points on target anatomy boundary (i.e., white dots on image (M) in FIG. 5) with transformation $T_{trx}$.

Thus, the transformation matrix $T_{trx}$ may be obtained. Step ⑩ may be included in step 112 of the method 100 shown in FIG. 1.

The optimization problem (i.e., minimizing the alignment cost) can, for example, be solved by the Gauss-Newton algorithm, for example in the same or a similar manner as illustrated by the pseudocode given below ("Algorithm 1: Optimization by Gauss-Newton method").

In the pseudocode, deltaR$_{trx}$ corresponds to $\delta R_{trx}$ above, and deltaC$_{trx}$ corresponds to $\delta C_{trx}$ above, and W denotes the warping of boundary points with transformation $T_{trx}$.

---

Algorithm 1: Optimization by Gauss-Newton method

--- input : i) distance map (J), ii) sampled mask contour pixels x from (M) and iii) the coarse scale factor ws$_{trx}$ initial shifts (deltaR$_{trx}$, deltaC$_{trx}$) of x with respect to (J)
output: a transformation matrix $T_{trx}$
1 optimization target: $\arg\min_{\Delta p} \Sigma J(W(x, T_{trx} + \Delta p))$;
2 initialization: compute the gradient $\nabla J$ of the distance map (J) along the horizontal and vertical directions, $$T_{trx} = \begin{pmatrix} ws_{trx} & 0 & deltaC_{trx} \\ 0 & 1 & deltaR_{trx} \end{pmatrix},$$

iteration = 0;
3 while iteration <= 30 and $|\Delta p|$ > epsilon do
4 |  Warp contour pixels: $x_{itr} = W(x, T_{trx})$;

5 |  Evaluate $\dfrac{\partial W}{\partial p}$ at $x_{itr}$: $\begin{pmatrix} x_{itr} & 0 & 1 & 0 \\ 0 & y_{xtr} & 0 & 1 \end{pmatrix}$;

6 |  Compute $\nabla J \dfrac{\partial W}{\partial p}$ at $x_{itr}$;

7 |  Compute $\sum \left[ \nabla J \dfrac{\partial W}{\partial p} \right]^T \left[ \nabla J \dfrac{\partial W}{\partial p} \right]$;

8 |  Compute $\sum \left[ \nabla J \dfrac{\partial W}{\partial p} \right]^T J$ at $x_{itr}$;

9 |  Compute $\Delta p = \left( \sum \left[ \nabla J \dfrac{\partial W}{\partial p} \right]^T \left[ \nabla J \dfrac{\partial W}{\partial p} \right] \right)^{-1} \left( \sum \left[ \nabla J \dfrac{\partial W}{\partial p} \right]^T J \right)$;

10 |  Update $T_{trx} = T_{trx} - \Delta p$;
11 |  iteration = iteration + 1
12 end

---

From SAG to TRX: (Lower Half of Diagram 500)

These steps are similar to the ones for the upper half of the diagram 500 but are done from SAG to TRX.

Step ⑪: Extract the optimal real SAG view segmentation mask (Q) with shape of ($H_{sag}$, $W_{sag}$) from the stack of SAG segmentation masks (D) with (overall) shape of ($H_{sag}$, $W_{sag}$, $N_{sag}$). This step is similar to step ②. Step ⑪ may be included in step 114 of the method 100 shown in FIG. 1.

Step ⑫: Generate the signed distance map (T) based on the mask boundary of (Q). The distance map generation algorithm is the same as the one used in ③. Step ⑫ may be included in step 118 of the method 100 shown in FIG. 1.

Step ⑬: Extract the optimal simulated SAG view segmentation mask (P) with shape of ($H_{trx}$, $N_{trx}$) from the stack of TRX segmentation masks (C) with (overall) shape of ($H_{trx}$, $W_{trx}$, $N_{trx}$). The optimal frame extraction algorithm is the same as that in the step ⑤. Step ⑬ may be included in step 116 of the method 100 shown in FIG. 1.

Step ⑭: Estimate the coarse scale factor $ws_{sag}$ of the simulated SAG mask (P) along its width direction. Then resize (P) to (R) based on $ws_{sag}$. The coarse estimation is based on the fact that the width over height ratio (WoH) of the thyroid in the real SAG frame (Q) and the simulated SAG frame (P) should be the same. Step ⑭ may be included in step 118 of the method 100 shown in FIG. 1.

Step ⑮: Extract and sample the boundary pixels (contour pixels) (V) from the selected simulated SAG thyroid segmentation mask (R) similar to step ⑦. In (V), the sampled pixels are shown as white dots. Step ⑮ may be included in step 118 of the method 100 shown in FIG. 1.

Step ⑯: Sample regional anchor pixels (U) for (R). The sample strategy is the same as that used in the step ⑧. In (U), the sampled pixels are shown as white dots. Step ⑯ may be included in step 118 of the method 100 shown in FIG. 1.

Step ⑰: Estimate the coarse shifts ($\delta R_{sag}$, $\delta C_{sag}$) between thyroid mask in (T) and that in (Q) by maximizing the alignment response computed upon (U) and (T). This step is the same as the one used in step ⑨. Step ⑰ may be included in step 118 of the method 100 shown in FIG. 1.

Step ⑱: Estimate the scale and translation between the segmentation mask in (R) and that in (Q) by minimizing the alignment cost defined as the sum of square distance with respect to the transformation matrix $T_{sag}$, using following formula (5):

$$\arg\min_{T_{sag}} \Sigma S(W((x|V(x)==1), T_{sag})) \qquad (5)$$

where S is distance map (see FIG. 6) and W is the warping of the points on target anatomy boundary (i.e. white dots on image (V) in FIG. 5) with transformation $T_{sag}$.

The optimization problem is solved by the same algorithm as used in step ⑩. Thus, the transformation matrix $T_{sag}$ may be obtained. Step ⑱ may be included in step 120 of the method 100 shown in FIG. 1.

Final Mapping Equations

With $T_{trx}$ and $T_{sag}$ computed, any point from the TRX sweep (frame index $idx_{trx}$ and coordinates ($x_{trx}$, $y_{trx}$)) can be mapped to the corresponding point on the SAG sweep (frame index $idx_{sag}$ and coordinates $(x_{sag}, y_{sag})$) using the following equations (6) to (7):

Mapping from TRX $(idx_{trx}, y_{trx}, x_{trx})$ to SAG $(idx_{sag}, y_{sag}, x_{sag})$:

$$idx_{sag}=int((x_{trx}-T_{trx}(2,3))/(T_{trx}(1,1)*ws_{trx})+0.5)$$

$$y_{sag}=int((y_{trx}-T_{trx}(2,3))/T_{trx}(2,2)+0.5)$$

$$x_{sag}=int(idx_{trx}*ws_{sag}*T_{sag}(1,1)+T_{sag}(2,3)+0.5) \quad (6)$$

Mapping from SAG $(idx_{sag}, y_{sag}, x_{sag})$ to TRX $(idx_{trx}, y_{trx}, x_{trx})$:

$$idx_{trx}=int((x_{sag}-T_{sag}(2,3))/(T_{sag}(1,1)*ws_{sag})+0.5)$$

$$y_{trx}=int(y_{sag}*T_{trx}(2,2)+T_{trx}(2,3)+0.5)$$

$$x_{trx}=int(idx_{sag}*ws_{trx}*T_{trx}(1,1)+T_{trx}(2,3)+0.5) \quad (7)$$

This may be included in step 122 of the method 100 shown in FIG. 1. Thus, cross-referencing between the two views may be achieved. Illustratively, equation (6) corresponds to an embodiment of equation (1) above, and equation (7) corresponds to an embodiment of equation (2) above.

Figure 6:
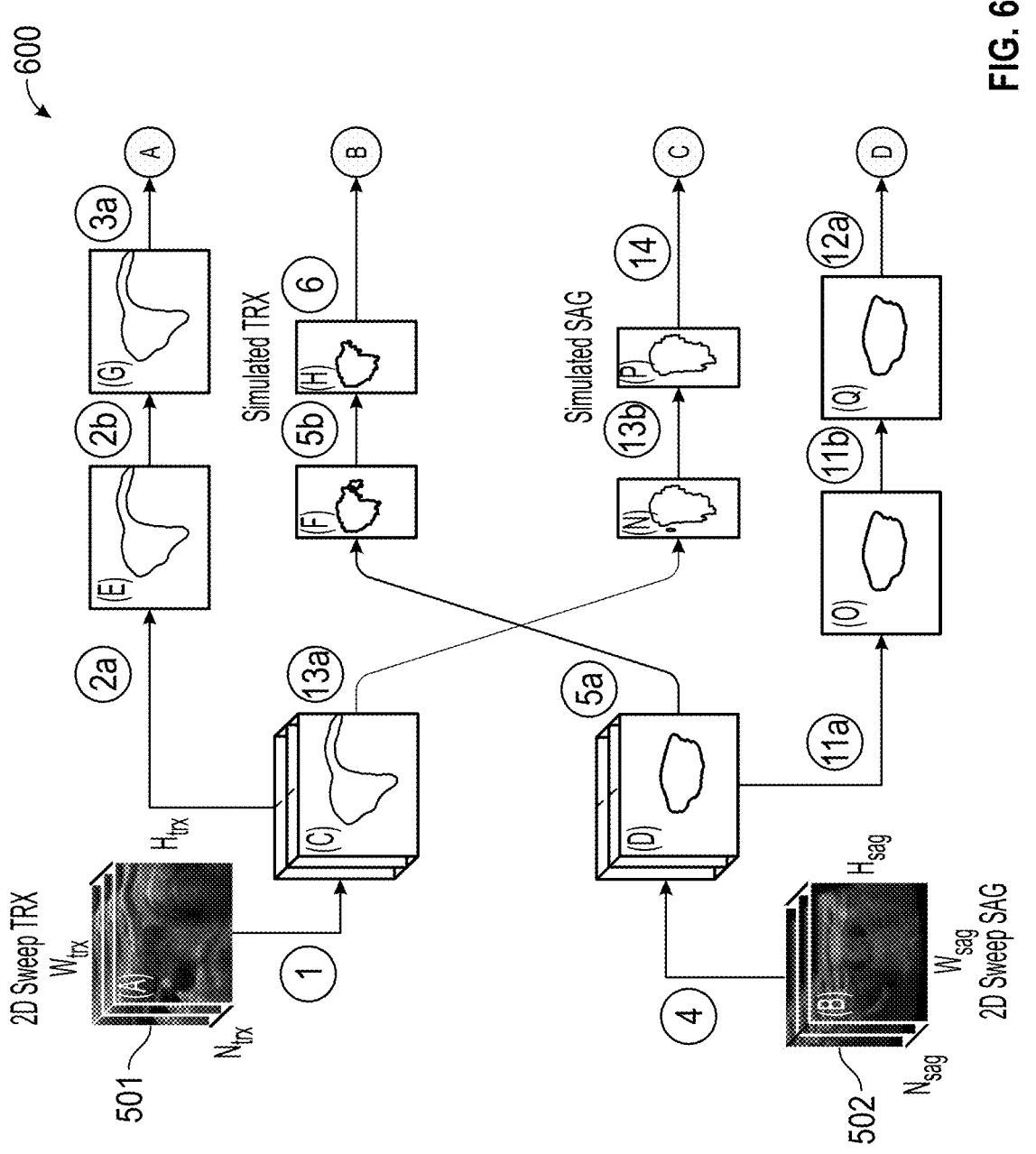
FIG. 6 depicts another flow diagram illustrating aspects of a method for cross-referencing of 2D ultrasound scans of a tissue volume according to various embodiments of the present invention.
Figure 6:
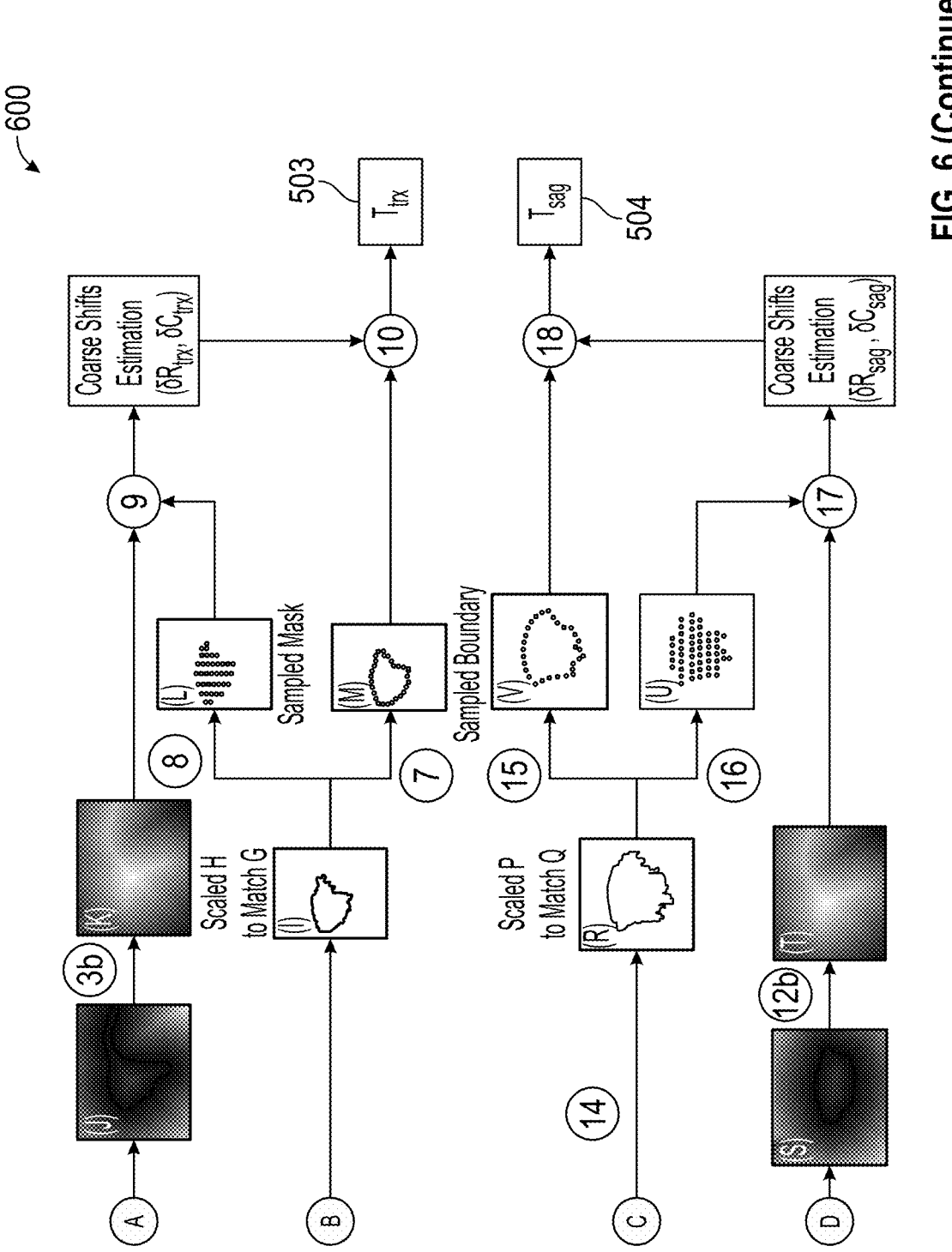
Figure 7:
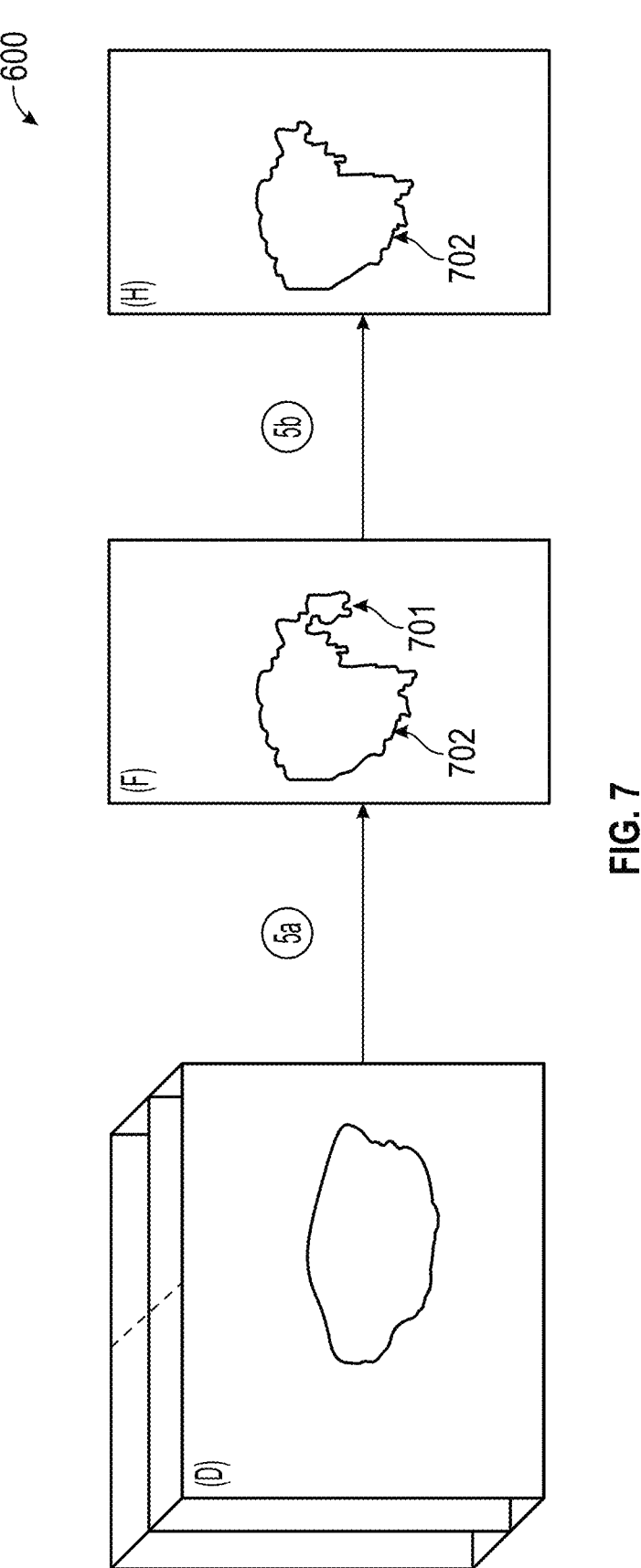
FIG. 7 illustrates a portion of the flow diagram shown in FIG. 6 in greater detail.
Figure 8:
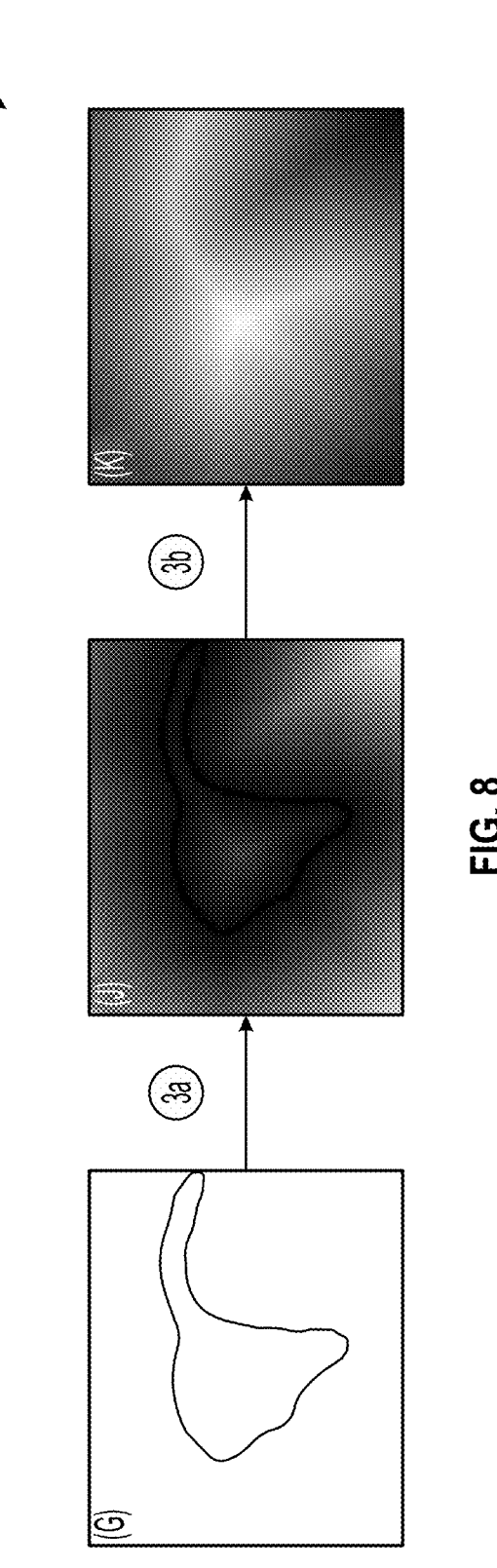
FIG. 8 illustrates another portion of the flow diagram shown in FIG. 6 in greater detail.

FIG. 6 shows another flow diagram 600 illustrating aspects of a method for cross-referencing 2D ultrasound scans in accordance with various embodiments (for example, the method 100 shown in FIG. 1), and FIG. 7 and FIG. 8 illustrate portions of the flow diagram shown in FIG. 6 in greater detail.

The flow diagram 600 is to some extent similar to the flow diagram 500 shown in FIG. 5, and in particular steps and stages in the flow diagram 600 having the same reference signs or labels as those shown in the flow diagram 500 in FIG. 5, are the same as those in the flow diagram 500 and will not be described in detail again here. Instead, the differences compared to the flow diagram 500 shown in FIG. 5 will mainly be described in the following.

With reference to FIG. 6 and FIG. 7, in the flow diagram 600, step ⑤ (of flow diagram 500) may include steps (5a) and (5b), such that transition from stage (D) to stage (H) leads through intermediate stage (F). FIG. 7 shows that intermediate stage (F), obtained upon step (5a) and corresponding to the largest simulated TRX segmentation mask from the sagittal (SAG) segmentation sweep, includes a (small) false positive region (denoted by reference sign 701), that is, a region in the segmentation mask (F) that is wrongly marked as corresponding to the target anatomy (thyroid lobe). This false positive region 701 can be removed by post-processing.

Due to the structure complexity of the thyroid region and the relatively low signal-noise ratio of ultrasound images, there may sometimes be false positive thyroid segmentation regions (such as region 701 in FIG. 7) in the selected frame. In various embodiments, and as shown in step (5b), a largest continuous component searching algorithm may be used to exclude these small regions that are not connected to the main thyroid segmentation (region 702 in FIG. 7) in the selected thyroid segmentation mask. That is, in step (5b), the largest continuous component of the mask (also referred to as largest contiguous component, largest connected component, or largest cluster) may be obtained, and noise thus may be removed. Largest continuous component searching algorithms are known as such in the art of image processing and thus will not be described in detail here. As a non-limiting example of such algorithm, the so-called OpenCV cv2.connectedComponentsWithStats algorithm may be used.

In a similar manner as described above for step ⑤, step ⑬ may include steps (13a) and (13b) in flow diagram 600, with step (13a) yielding the largest simulated SAG segmentation mask from the transverse (TRX) segmentation sweep (stage (N) in the flow diagram 600), and step (13b) yielding the largest component of the mask (stage (P) in the flow diagram 600).

Again, in a similar manner as described above for step ⑤, step ② may include steps (2a) and (2b) in flow diagram 600, with step (2a) yielding the largest TRX segmentation mask from the transverse (TRX) segmentation sweep (stage (E) in the flow diagram 600), and step (2b) yielding the largest component of the mask (stage (G) in the flow diagram 600).

Finally, in a similar manner as described above for step ⑤, step ⑪ may include steps (11a) and (11b) in flow diagram 600, with step (11a) yielding the largest SAG segmentation mask from the sagittal (SAG) segmentation sweep (stage (O) in the flow diagram 600), and step (11b) yielding the largest component of the mask (stage (Q) in the flow diagram 600).

Thus, the method illustrated in flow diagram 600 may include further refining the binary segmentation masks (E), (F), (N), and (O) obtained from the TRX and SAG sweep.

With reference to FIG. 6 and FIG. 8, in the flow diagram 600, step ③ (of flow diagram 500) may include steps (3a) and (3b), such that transition from stage (G) to stage (K) leads through intermediate stage (J).

In step (3a), the distance map (J) may be generated based on the mask boundary of the binary segmentation mask (G). Given the binary segmentation mask (G), the contours of the mask may be searched by a suitable contour searching algorithm, which may be known as such in the art. Then the longest contour may be kept. The distance map (J) may be generated based on this longest contour. The value of each pixel in the distance map (J) is the distance from the pixel to its closest contour pixel. The points on the contour boundary have zero values in the distance map.

In step (3b), the distance map (J) may be converted to the signed distance map (K). To obtain the signed distance map (K), the binary segmentation mask (G) may firstly be converted to a signed map, in which thyroid and non-thyroid pixels may be with values −1 and 1 rather than 0 and 1. The signed distance map (K) may then be generated by element-wise multiplication of the signed (G) and the distance map (J).

In a similar manner as described above for step ③, step ⑫ may include steps (12a) and (12b) in flow diagram 600, with step (12a) generating the distance map (S) based on the mask boundary of the binary segmentation mask (Q), and step (12b) converting the distance map (S) to the signed distance map (T).

In accordance with various embodiments, one or more of the following steps may optionally be included in the flow diagram 500 or in the flow diagram 600 to further enhance the cross-referencing:

In an optional step ⑲ (not shown), the in-plane shift between the real and simulated images may be further refined using the initial transformation matrices $T_{sag}$ and $T_{trx}$.

The step may include finding per-frame in-plane shifts $(RC_{trx}$ with shape of $(2, N_{trx}))$ of the simulated TRX frames with respect to their corresponding real TRX frames. Ideally, the scan trajectories of both TRX and SAG sweeps are supposed to be straight. However, it may be difficult for sonographers and radiologists to strictly follow a straight line when scanning the TRX sweeps. Therefore, a module for estimating per-frame in-plane shifts of TRX frames may be added to refine the registration of each pair of real and simulated TRX frames.

Particularly, for each TRX segmentation mask ((E') with shape of ($H_{trx}$, $W_{trx}$)), its corresponding simulated TRX mask ((F') with shape of ($H_{sag}$, $N_{sag}$)) may be retrieved by the last part of equation (6).

Then (G') and (L') may be obtained following step (2b) and ⑧ respectively. Then the shifts of the TRX frame (F') with respect to its corresponding real TRX frame (E') may be obtained by conducting the heuristic search algorithm based alignment of (G') and (L'), which is similar to the algorithm used in step ⑨ (here, the signed distance map (K) is replaced by the binary mask (G')).

Based on the in-plane shifts ($RC_{trx}$), the $RC_{sag}$ of the real SAG frames with respect to their corresponding simulated SAG frames may then be obtained for the inverse transformation.

In another optional step ⑳ (not shown), the $T_{sag}$ obtained in step ⑱ may be refined by conducting the intensity-based Lucas-Kanade algorithm. This step is to reduce the probable aperture problem caused by the sweeps with incomplete target anatomy scan (e.g., thyroid is too long in vertical direction to be covered by one frame in SAG view). To reduce the influence of this issue, the corresponding images ((N') and (O')) of the simulated SAG mask (N) and the real SAG mask (O) may be extracted from (A) and (B) first. Then, (N') may be resized to (R') along its width direction with scale factor $ws_{sag}$. The $T_{sag}$ may be refined by optimizing the sum of square difference of the two images (N') and (O'), using the following formula:

$$\arg\min_{T_{sag}} \Sigma \; [O'(W\,(x,\,T_{sag}))-N'(x)]^2 \qquad (8)$$

If optional steps ⑲ and ⑳ are performed, then refined cross-referencing equations are as follows.

Final Mapping Equations (With Additional Steps ⑲ and ⑳)

With steps ⑲ and ⑳, ($ws_{trx}$, $T_{trx}$, $RC_{trx}$) and ($ws_{sag}$, $T_{sag}$, $RC_{sag}$) are obtained. Then, any point from TRX sweep (frame index $idx_{trx}$ and coordinates ($x_{trx}$, $y_{trx}$)) can be mapped to the corresponding point on the SAG sweep (frame index $idx_{sag}$ and ($x_{sag}$, $y_{sag}$)) using the following equations:

Mapping from TRX ($idx_{trx}$, $y_{trx}$, $x_{trx}$) to SAG ($idx_{sag}$, $y_{sag}$, $x_{sag}$):

$$idx_{sag}=int((x_{trx}-T_{trx}(2,3)-RC_{trx}[1, \qquad idx_{trx}]/ \\ (T_{trx}(1,1)*ws_{trx})+0.5)$$

$$y_{sag}=int((y_{trx}-T_{trx}(2,3)-RC_{trx}[0,\;idx_{trx}])/T_{trx}(2,2)+0.5)$$

$$x_{sag}=int(idx_{trx}*ws_{sag}*T_{sag}(1,1)+T_{sag}(2,3)+0.5) \qquad (9)$$

Mapping from SAG ($idx_{sag}$, $y_{sag}$, $x_{sag}$) to TRX ($idx_{trx}$, $y_{trx}$, $x_{trx}$)

$$idx_{trx}=int((x_{sag}-T_{sag}(2,3))/(T_{sag}(1,1)*ws_{sag})+0.5)$$

$$y_{trx}=int(y_{sag}*T_{trx}(2,2)+T_{trx}(2,3)+RC_{sag}[0,\;x_{sag}]+0.5)$$

$$x_{trx}=int(idx_{sag}*ws_{trx}*T_{trx}(1,1)+T_{trx}(2,3)+RC_{sag}[1, \\ x_{sag}]+0.5) \qquad (10)$$

Illustratively, equation (9) corresponds to another embodiment of equation (1) above, and equation (10) corresponds to another embodiment of equation (2) above. Thus, cross-referencing between the two views (TRX and SAG) may be achieved.

Figure 9:
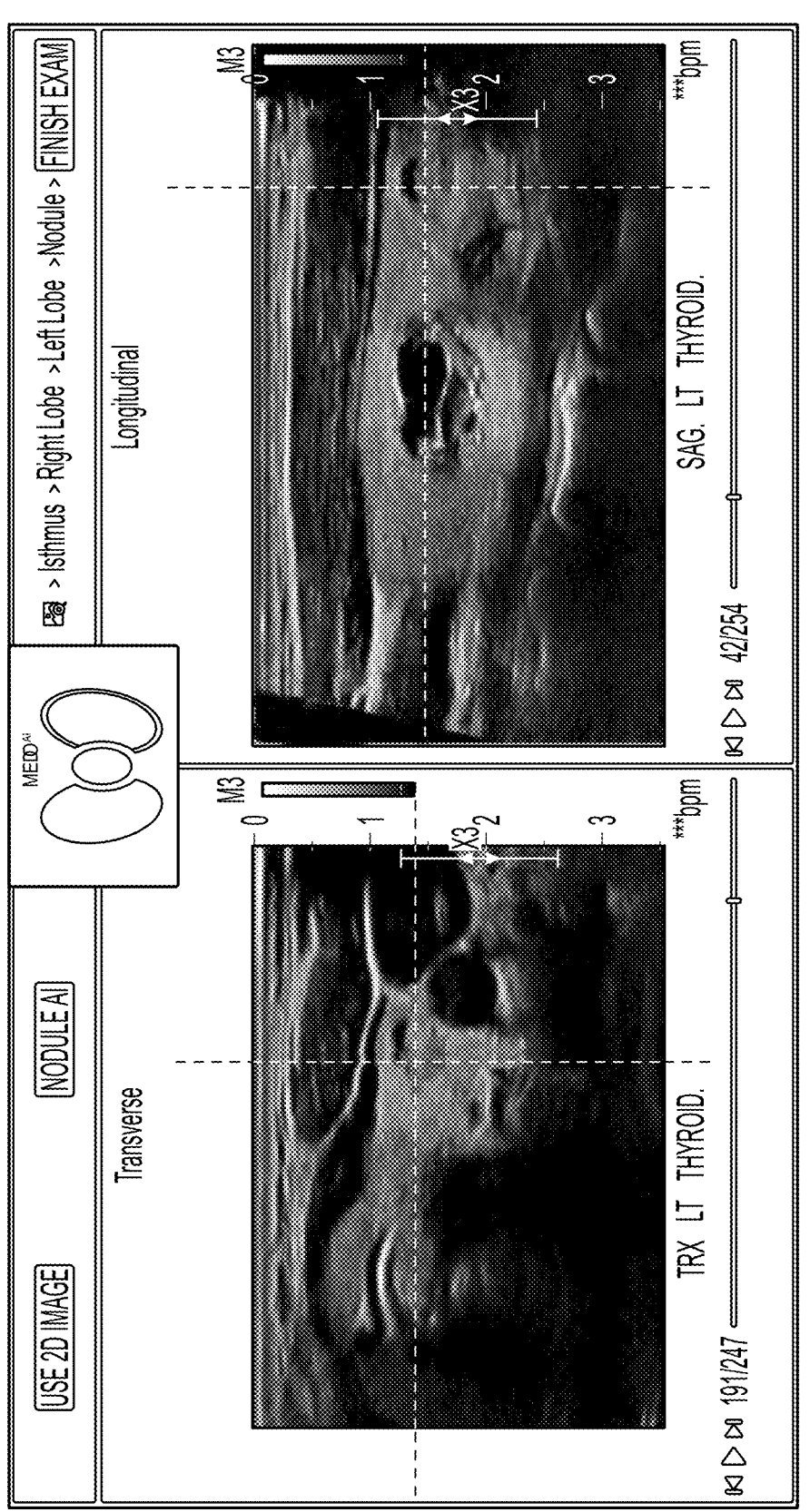
FIG. 9 depicts a screenshot of the cross-referencing tool or system from first view to second view according to various embodiments of the present invention.

FIG. 9 depicts a screenshot of the cross-referencing tool or system from first view to second view according to various embodiments of the present invention: by selecting any point on transverse scan (e.g. the cursor indicator on a thyroid nodule on the lower lobe of thyroid gland on the transverse view (point P1) on the left panel), the cross-referencing tool or system locates the corresponding nodule on sagittal scan (i.e. point P2 with corresponding x,y location and frame number in the sagittal sweep on the right panel).

Figure 10:
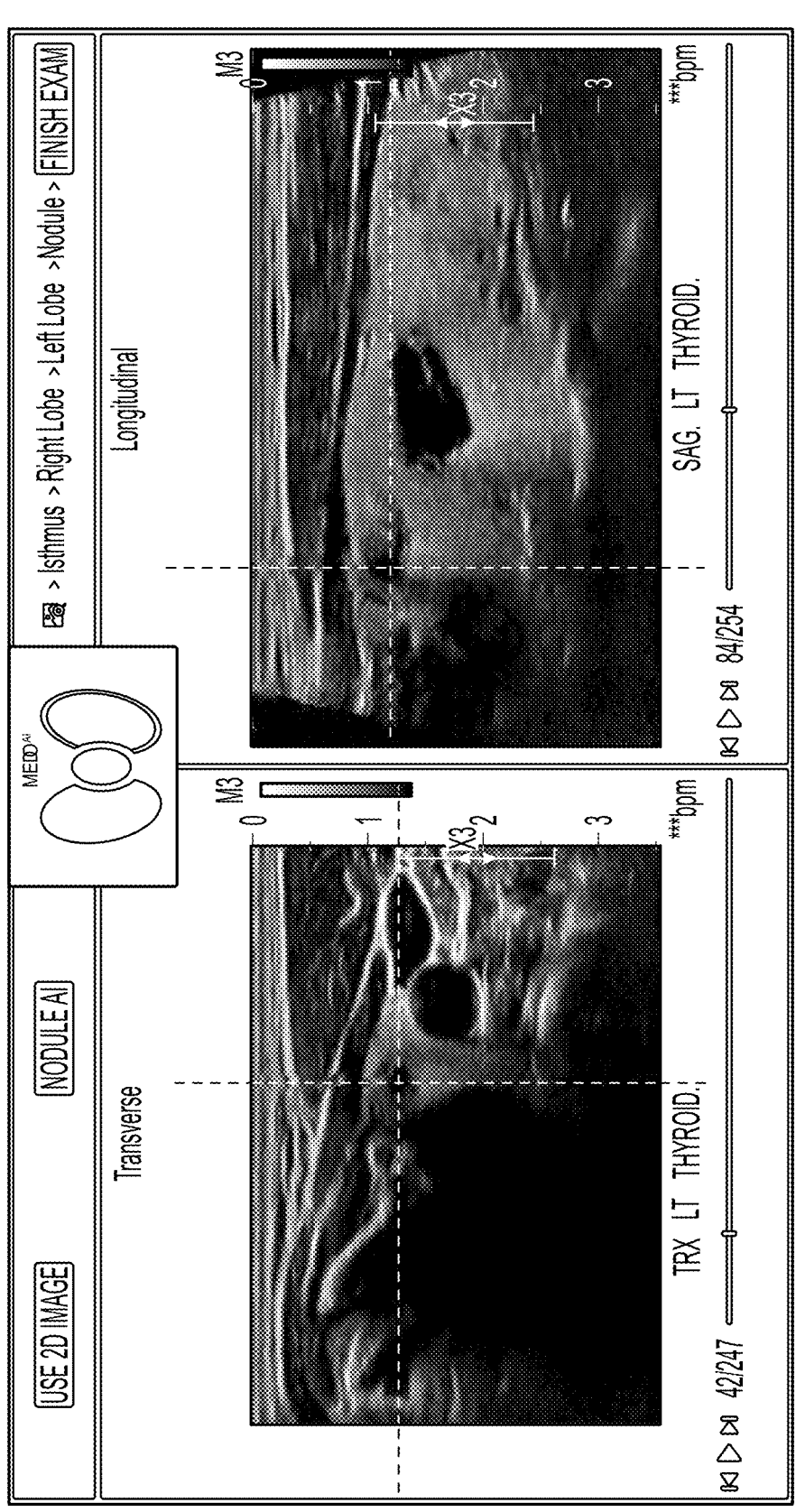
FIG. 10 depicts a screenshot of the cross referencing system from second view to first view according to various embodiments of the present invention.

FIG. 10 depicts a screenshot of the cross referencing system from second view to first view according to various embodiments of the present invention: by selecting another thyroid nodule on the upper lobe of thyroid gland on the sagittal sweep (point P3 on the right panel), the cross-referencing tool locates that nodule (corresponding x,y location and frame number) in the transverse sweep (point P4 on the left panel).

In accordance with an aspect of the present invention, there are provided a method and a system for cross-referencing of ultrasound sweeps from two orthogonal planes based on segmentation masks.

In accordance with another aspect of the present invention, there is provided a non-transitory computer readable storage medium with instructions to be executed by a processor to: receive a pair of ultrasound scans; apply the pair of ultrasound scans to a sequence of transformations and post-processing; and produce transformation mappings from the paired two scans to form a final probability segmentation.

In accordance with various embodiments, a (computer-implemented) method or algorithm may be provided that may compute a transformation that outputs a particular frame index and coordinate within a second view (e.g., sagittal view), based on a frame index and coordinates provided by a user on a first view (e.g., transverse view). The algorithm may use a linear transformation to place a transverse-image and sagittal-image pair into the same spatial coordinate system. This may allow the user to locate regions of interest (e.g., nodules) in a sagittal image using regions of interest defined in a transverse image.

In accordance with various embodiments, redundancy of two perpendicular freehand ultrasound sweep acquisitions may be exploited: the out-of-plane distances in one sweep can be accurately recovered from another sweep because they appear in-plane. In order to do this, various embodiments provide a method to register these two acquisitions.

In accordance with various embodiments, a cross-referencing module may be provided that computes two transformation matrices and then maps any frame index and coordinates provided by a user on a transverse image to frame index and coordinates within a sagittal (longitudinal) image.

The mapping is based on the two transformation matrices and may be used to place a transverse-image and sagittal-image pair into the same spatial coordinate system, allowing transverse-view points to be mapped to sagittal-view points and vice versa.

While embodiments of the invention have been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method for cross-referencing of two-dimensional (2D) ultrasound scans of a tissue volume, the method comprising:

generating a first series of 2D ultrasound images of a tissue volume associated with a first plurality of positions, respectively, along a first scanning direction of the tissue volume, the tissue volume including a target anatomy;

generating a second series of 2D ultrasound images of the tissue volume associated with a second plurality of positions, respectively, along a second scanning direction of the tissue volume, wherein the second scanning direction is at least substantially orthogonal to the first scanning direction;

generating a first 2D representation of the target anatomy from the first series of 2D ultrasound images, the first 2D representation associated with one of the images of the first series of 2D ultrasound images;

generating a first simulated 2D representation, different from the first 2D representation, of the target anatomy from the second series of 2D ultrasound images, wherein the first simulated 2D representation is a projection of the second series of 2D ultrasound images onto a plane of the first series of 2D ultrasound images such that the first simulated 2D representation and the first 2D representation of the target anatomy correspond to one another in terms of viewing direction onto the target anatomy;

processing the first 2D representation and the first simulated 2D representation of the target anatomy so as to at least substantially match pixel positions associated with the target anatomy in the first simulated 2D representation with pixel positions associated with the target anatomy in the first 2D representation;

determining a first transformation matrix from the processed first 2D representation and the processed first simulated 2D representation of the target anatomy, the first transformation matrix including a first scale and translation parameter for mapping the processed first 2D representation to the processed first simulated 2D representation;

generating a second 2D representation of the target anatomy from the second series of 2D ultrasound images, the second 2D representation associated with one of the images of the second series of 2D ultrasound images;

generating a second simulated 2D representation, different from the second 2D representation, of the target anatomy from the first series of 2D ultrasound images, wherein the second simulated 2D representation is a projection of the first series of 2D ultrasound images onto a plane of the second series of 2D ultrasound images such that the second simulated 2D representation and the second 2D representation of the target anatomy correspond to one another in terms of viewing direction onto the target anatomy;

processing the second 2D representation and the second simulated 2D representation of the target anatomy so as to at least substantially match pixel positions associated with the target anatomy in the second simulated 2D representation with pixel positions associated with the target anatomy in the second 2D representation;

determining a second transformation matrix from the processed second 2D representation and the processed second simulated 2D representation of the target anatomy, the second transformation matrix including a second scale and translation parameter for mapping the processed second 2D representation to the processed second simulated 2D representation; and using the first transformation matrix and the second transformation matrix to determine, for a first location associated with the target anatomy in the second series of 2D ultrasound images, a corresponding second location associated with the target anatomy in the first series of 2D ultrasound images, including applying a first function of the first transformation matrix and second transformation matrix to pixel coordinates corresponding to the first location so as to obtain pixel coordinates corresponding to the second location.

2. The method of claim 1, further comprising:

using the first transformation matrix and the second transformation matrix to determine, for a third location associated with the target anatomy in the first series of 2D ultrasound images, a corresponding fourth location associated with the target anatomy in the second series of 2D ultrasound images.

3. The method of claim 2, wherein using the first transformation matrix and the second transformation matrix to determine the fourth location comprises:

applying a second function of the first transformation matrix and second transformation matrix to pixel coordinates corresponding to the third location so as to obtain pixel coordinates corresponding to the fourth location.

4. The method of claim 1, further comprising:

generating a first plurality of binary segmentation masks from the first series of 2D ultrasound images, each binary segmentation mask of the first plurality of binary segmentation masks corresponding to a respective one of the 2D ultrasound images of the first series of 2D ultrasound images; and generating a second plurality of binary segmentation masks from the second series of 2D ultrasound images, each binary segmentation mask of the second plurality of binary segmentation masks corresponding to a respective one of the 2D ultrasound images of the second series of 2D ultrasound images, wherein the first 2D representation of the target anatomy is generated from one of the binary segmentation masks of the first plurality of binary segmentation masks, and wherein the second 2D representation of the target anatomy is generated from one of the binary segmentation masks of the second plurality of binary segmentation masks.

5. The method of claim 4, wherein:

the first 2D representation of the target anatomy corresponds to a largest binary segmentation mask among the first plurality of binary segmentation masks; and the second 2D representation of the target anatomy corresponds to a largest binary segmentation mask among the second plurality of binary segmentation masks.

6. The method of claim 4, wherein:

generating the first simulated 2D representation of the target anatomy from the second series of 2D ultrasound images comprises generating the first simulated 2D representation of the target anatomy from the second plurality of binary segmentation masks; and generating the second simulated 2D representation of the target anatomy from the first series of 2D ultrasound images comprises generating the second simulated 2D representation of the target anatomy from the first plurality of binary segmentation masks.

7. The method of claim 4, wherein:

processing the first 2D representation comprises generating a first signed distance map from the first 2D representation; and processing the second 2D representation comprises generating a second signed distance map from the second 2D representation.

8. The method of claim 7, wherein:

processing the first simulated 2D representation comprises scaling a width of the first simulated 2D representation so as to match a width of the first 2D representation; and processing the second simulated 2D representation comprises scaling a width of the second simulated 2D representation so as to match a width of the second 2D representation.

9. The method of claim 8, wherein:

processing the first simulated 2D representation further comprises determining and sampling contour pixels associated with a contour of the target anatomy from the scaled first simulated 2D representation, and processing the second simulated 2D representation further comprises determining and sampling contour pixels associated with a contour of the target anatomy from the scaled second simulated 2D representation.

10. The method of claim 9, wherein:

processing the first simulated 2D representation further comprises sampling a first subset of pixels from the scaled first simulated 2D representation; and processing the second simulated 2D representation further comprises sampling a second subset of pixels from the scaled second simulated 2D representation.

11. The method of claim 10, wherein:

processing the first simulated 2D representation further comprises estimating coarse shifts between the scaled first simulated 2D representation and the first 2D representation using the first signed distance map and the first sampled subset of pixels; and processing the second simulated 2D representation further comprises estimating coarse shifts between the scaled second simulated 2D representation and the second 2D representation using the second signed distance map and the sampled second subset of pixels.

12. The method of claim 11, wherein:

determining the first transformation matrix comprises estimating a scale and translation between the scaled first simulated 2D representation and the first 2D representation by minimizing a first alignment cost defined as a first cost function with respect to the first transformation matrix; and determining the second transformation matrix comprises estimating a scale and translation between the scaled second simulated 2D representation and the second 2D representation by minimizing a second alignment cost defined as a second cost function with respect to the second transformation matrix.

13. The method of claim 1, wherein the first scanning direction corresponds to a transverse scan of the tissue volume and the second scanning direction corresponds to a sagittal scan of the tissue volume.

14. A system for cross-referencing of two-dimensional (2D) ultrasound scans of a tissue volume, the system comprising:

a memory; and at least one processor communicatively coupled to the memory, and configured to:

generate a first series of 2D ultrasound images of a tissue volume associated with a first plurality of positions, respectively, along a first scanning direction of the tissue volume, the tissue volume including a target anatomy;

generate a second series of 2D ultrasound images of the tissue volume associated with a second plurality of positions, respectively, along a second scanning direction of the tissue volume, wherein the second scanning direction is at least substantially orthogonal to the first scanning direction;

generate a first 2D representation of the target anatomy from the first series of 2D ultrasound images, the first 2D representation associated with one of the images of the first series of 2D ultrasound images;

generate a first simulated 2D representation, different from the first 2D representation, of the target anatomy from the second series of 2D ultrasound images, wherein the first simulated 2D representation is a projection of the second series of 2D ultrasound images onto a plane of the first series of 2D ultrasound images such that the first simulated 2D representation and the first 2D representation of the target anatomy correspond to one another in terms of viewing direction onto the target anatomy;

process the first 2D representation and the first simulated 2D representation of the target anatomy so as to at least substantially match pixel positions associated with the target anatomy in the first simulated 2D representation with pixel positions associated with the target anatomy in the first 2D representation;

determine a first transformation matrix from the processed first 2D representation and the processed first simulated 2D representation of the target anatomy, the first transformation matrix including a first scale and translation parameter for mapping the processed first 2D representation to the processed first simulated 2D representation;

generate a second 2D representation of the target anatomy from the second series of 2D ultrasound images, the second 2D representation associated with one of the images of the second series of 2D ultrasound images;

generate a second simulated 2D representation, different from the second 2D representation, of the target anatomy from the first series of 2D ultrasound images, wherein the second simulated 2D representation is a projection of the first series of 2D ultrasound images onto a plane of the second series of 2D ultrasound images such that the second simulated 2D representation and the second 2D representation of the target anatomy correspond to one another in terms of viewing direction onto the target anatomy;

process the second 2D representation and the second simulated 2D representation of the target anatomy so as to at least substantially match pixel positions associated with the target anatomy in the second simulated 2D representation with pixel positions associated with the target anatomy in the second 2D representation;

determine a second transformation matrix from the processed second 2D representation and the processed second simulated 2D representation of the target anatomy, the second transformation matrix including a second scale and translation parameter for mapping the processed second 2D representation to the processed second simulated 2D representation; and use the first transformation matrix and the second transformation matrix to determine for a first location associated with the target anatomy in the second series of 2D ultrasound images a corresponding second location associated with the target anatomy in the first series of 2D ultrasound images, including applying a first function of the first transformation matrix and second transformation matrix to pixel coordinates corresponding to the first location so as to obtain pixel coordinates corresponding to the second location.

15. The system of claim 14, wherein the at least one processor is further configured to:

use the first transformation matrix and the second transformation matrix to determine for a third location associated with the target anatomy in the first series of 2D ultrasound images a corresponding fourth location associated with the target anatomy in the second series of 2D ultrasound images.

16. The system of claim 15, wherein, when the at least one processor uses the first transformation matrix and the second transformation matrix to determine the fourth location, the at least one processor is configured to:

apply a second function of the first transformation matrix and second transformation matrix to pixel coordinates corresponding to the third location so as to obtain pixel coordinates corresponding to the fourth location.

17. The system of claim 14, wherein the at least one processor is further configured to:

generate a first plurality of binary segmentation masks from the first series of 2D ultrasound images, each binary segmentation mask of the first plurality of binary segmentation masks corresponding to a respective one of the 2D ultrasound images of the first series of 2D ultrasound images; and generate a second plurality of binary segmentation masks from the second series of 2D ultrasound images, each binary segmentation mask of the second plurality of binary segmentation masks corresponding to a respective one of the 2D ultrasound images of the second series of 2D ultrasound images, wherein the first 2D representation of the target anatomy is generated from one of the binary segmentation masks of the first plurality of binary segmentation masks, and wherein the second 2D representation of the target anatomy is generated from one of the binary segmentation masks of the second plurality of binary segmentation masks.

18. The system of claim 17, wherein the first 2D representation of the target anatomy corresponds to a largest binary segmentation mask among the first plurality of binary segmentation masks, and the second 2D representation of the target anatomy corresponds to a largest binary segmentation mask among the second plurality of binary segmentation masks.

19. The system of claim 14, wherein the first scanning direction corresponds to a transverse scan of the tissue volume and the second scanning direction corresponds to a sagittal scan of the tissue volume.

20. The system of claim 14, further comprising an ultrasound transducer communicatively coupled to the memory and the at least one processor, wherein the at least one processor is configured to:

generate the first series of 2D ultrasound images based on a first series of ultrasound waves acquired by the ultrasound transducer positioned at the first plurality of positions with respect to a first plurality of time instances; and generate the second series of 2D ultrasound images based on a second series of ultrasound waves acquired by the ultrasound transducer positioned at the second plurality of positions with respect to a second plurality of time instances.

21. A non-transitory computer-readable storage medium storing one or more programs the one or more programs comprising instructions, which when executed by at least one processor cause the at least one processor to perform a method for cross-referencing of two-dimensional (2D) ultrasound scans of a tissue volume, the method comprising:

generating a first series of 2D ultrasound images of a tissue volume associated with a first plurality of positions, respectively, along a first scanning direction of the tissue volume, the tissue volume including a target anatomy;

generating a second series of 2D ultrasound images of the tissue volume associated with a second plurality of positions, respectively, along a second scanning direction of the tissue volume, wherein the second scanning direction is at least substantially orthogonal to the first scanning direction;

generating a first 2D representation of the target anatomy from the first series of 2D ultrasound images, the first 2D representation associated with one of the images of the first series of 2D ultrasound images;

generating a first simulated 2D representation, different from the first 2D representation, of the target anatomy from the second series of 2D ultrasound images, wherein the first simulated 2D representation is a projection of the second series of 2D ultrasound images onto a plane of the first series of 2D ultrasound images such that the first simulated 2D representation and the first 2D representation of the target anatomy correspond to one another in terms of viewing direction onto the target anatomy;

processing the first 2D representation and the first simulated 2D representation of the target anatomy so as to at least substantially match pixel positions associated with the target anatomy in the first simulated 2D representation with pixel positions associated with the target anatomy in the first 2D representation;

determining a first transformation matrix from the processed first 2D representation and the processed first simulated 2D representation of the target anatomy, the first transformation matrix including a first scale and translation parameter for mapping the processed first 2D representation to the processed first simulated 2D representation;

generating a second 2D representation of the target anatomy from the second series of 2D ultrasound images, the second 2D representation associated with one of the images of the second series of 2D ultrasound images;

generating a second simulated 2D representation, different from the second 2D representation, of the target anatomy from the first series of 2D ultrasound images, wherein the second simulated 2D representation is a projection of the first series of 2D ultrasound images onto a plane of the second series of 2D ultrasound images such that the second simulated 2D representation and the second 2D representation of the target anatomy correspond to one another in terms of viewing direction onto the target anatomy;

processing the second 2D representation and the second simulated 2D representation of the target anatomy so as to at least substantially match pixel positions associated with the target anatomy in the second simulated 2D representation with pixel positions associated with the target anatomy in the second 2D representation;

determining a second transformation matrix from the processed second 2D representation and the processed second simulated 2D representation of the target anatomy, the second transformation matrix including a second scale and translation parameter for mapping the processed second 2D representation to the processed second simulated 2D representation; and using the first transformation matrix and the second transformation matrix to determine for a first location associated with the target anatomy in the second series of 2D ultrasound images a corresponding second location associated with the target anatomy in the first series of 2D ultrasound images, including applying a first function of the first transformation matrix and second transformation matrix to pixel coordinates corresponding to the first location so as to obtain pixel coordinates corresponding to the second location.

* * * * *